US011490942B2

(12) United States Patent
El Zoghbi et al.

(10) Patent No.: US 11,490,942 B2
(45) Date of Patent: Nov. 8, 2022

(54) DEVICE AND SYSTEM FOR FACILITATING INSERTION OF A BONE TREATMENT DEVICE

(71) Applicant: DEPUY SYNTHES PRODUCTS, INC., Raynham, MA (US)

(72) Inventors: Gaser El Zoghbi, Rombach (CH); This Aebi, Grenchen (CH); Henri Défossez, Neuchatel (CH); André Weber, Olten (CH); Robert Uehlinger, Solothurn (CH); John V. Hunt, Cincinnati, OH (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 551 days.

(21) Appl. No.: 16/674,406

(22) Filed: Nov. 5, 2019

(65) Prior Publication Data
US 2021/0128217 A1 May 6, 2021

(51) Int. Cl.
*A61B 17/90* (2006.01)
*A61B 17/88* (2006.01)
*A61B 17/92* (2006.01)

(52) U.S. Cl.
CPC .......... *A61B 17/90* (2021.08); *A61B 17/8872* (2013.01); *A61B 17/8897* (2013.01); *A61B 17/921* (2013.01); *A61B 17/8816* (2013.01)

(58) Field of Classification Search
CPC ........ A61B 2017/0268; A61B 17/1717; A61B 17/3417; A61B 17/3468; A61B 17/3472;
(Continued)

(56) References Cited

U.S. PATENT DOCUMENTS 5,507,751 A 4/1996 Goode et al.
8,956,284 B2 2/2015 Gorek et al.
(Continued)

OTHER PUBLICATIONS

Tajima et al., "A Heart-shaped Sleeve Simplifies Intramedullary Tibial Nail Insertion when Using the Suprapatellar Approach", the $3^{rd}$ AO Trauma Asia Pacific Scientific Congress and TK Experts' Symposium, Jul. 2017, 7 sheets.
(Continued)

*Primary Examiner* — Larry E Waggle, Jr.
(74) *Attorney, Agent, or Firm* — Fay Kaplun & Marcin, LLP

(57) ABSTRACT

A device includes an outer sleeve of flexible material forming an outer conduit extending longitudinally therethrough for the insertion of a bone treatment device ("BTD") to target sites within a living body. A distal opening of the outer conduit is open so that, when the outer sleeve is in a desired position within the body, BTD is inserted through the outer conduit exits the outer sleeve adjacent to a target portion of a bone. The device also includes an inner sleeve received within the outer sleeve and defining an inner conduit within the outer conduit to form a protective covering. The inner sleeve is split longitudinally. Portions of the inner sleeve on opposite sides of the split are coupled to one another so that a diameter of the inner conduit is adjustable in response to forces exerted thereon by one of BTD and tissues surrounding the outer sleeve.

18 Claims, 17 Drawing Sheets

(58) Field of Classification Search
CPC .... A61B 17/8872; A61B 17/90; A61B 17/921
See application file for complete search history.

(56) References Cited

U.S. PATENT DOCUMENTS

| | | |
|---|---|---|
| 9,101,432 B2 | 8/2015 | Limouze et al. |
| 9,138,278 B2 | 9/2015 | Van Osten, III |
| 9,968,368 B2 | 5/2018 | Okuno et al. |
| 2013/0310886 A1* | 11/2013 | VanOsten .......... A61B 17/1717 606/329 |
| 2014/0081281 A1 | 3/2014 | Felder |
| 2018/0353193 A1* | 12/2018 | Hirsch .................. A61B 17/56 |

OTHER PUBLICATIONS

"Technique Guide: DePuy Synthes Suprapatellar Instrumentation for Expert Tibial Nail", Jun. 2016, 76 sheets.

\* cited by examiner

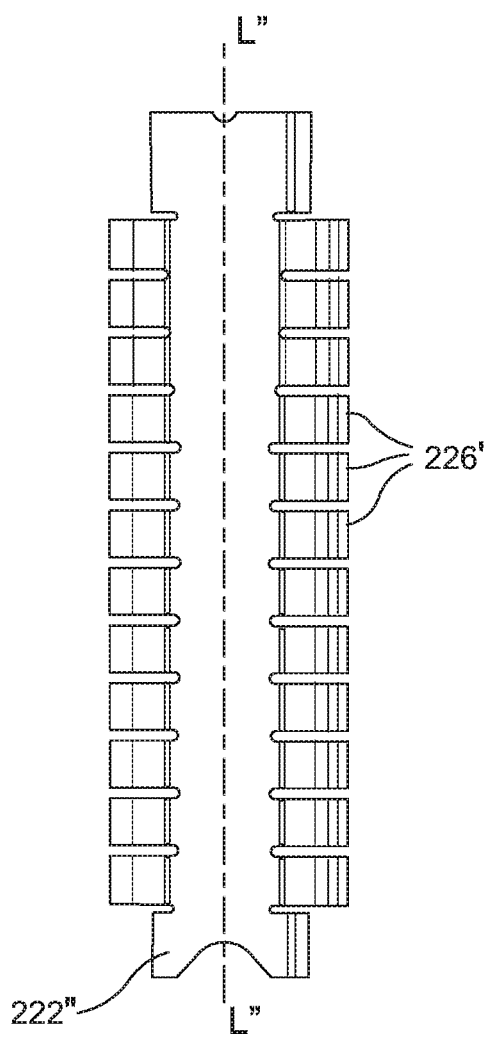
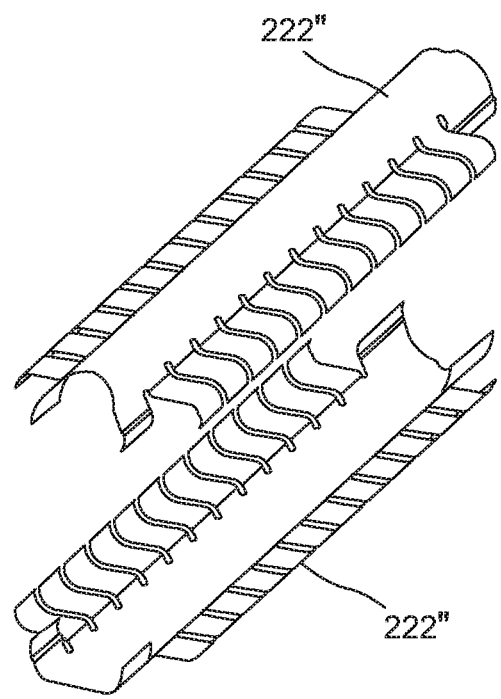
FIG. 19   FIG. 20
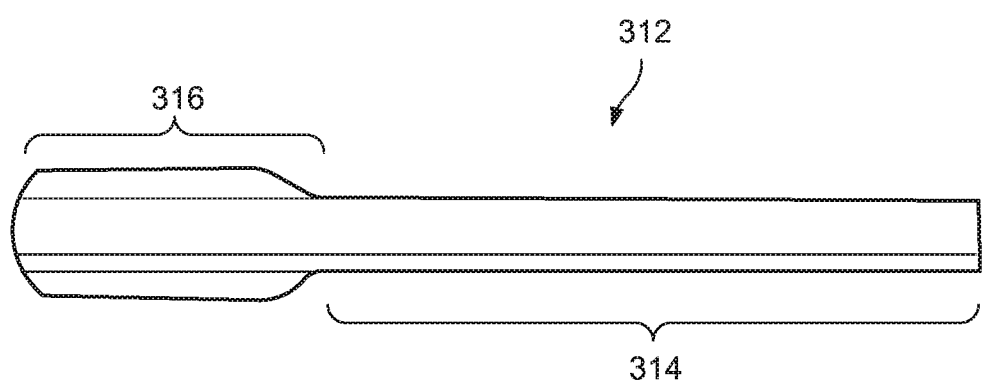
FIG. 21

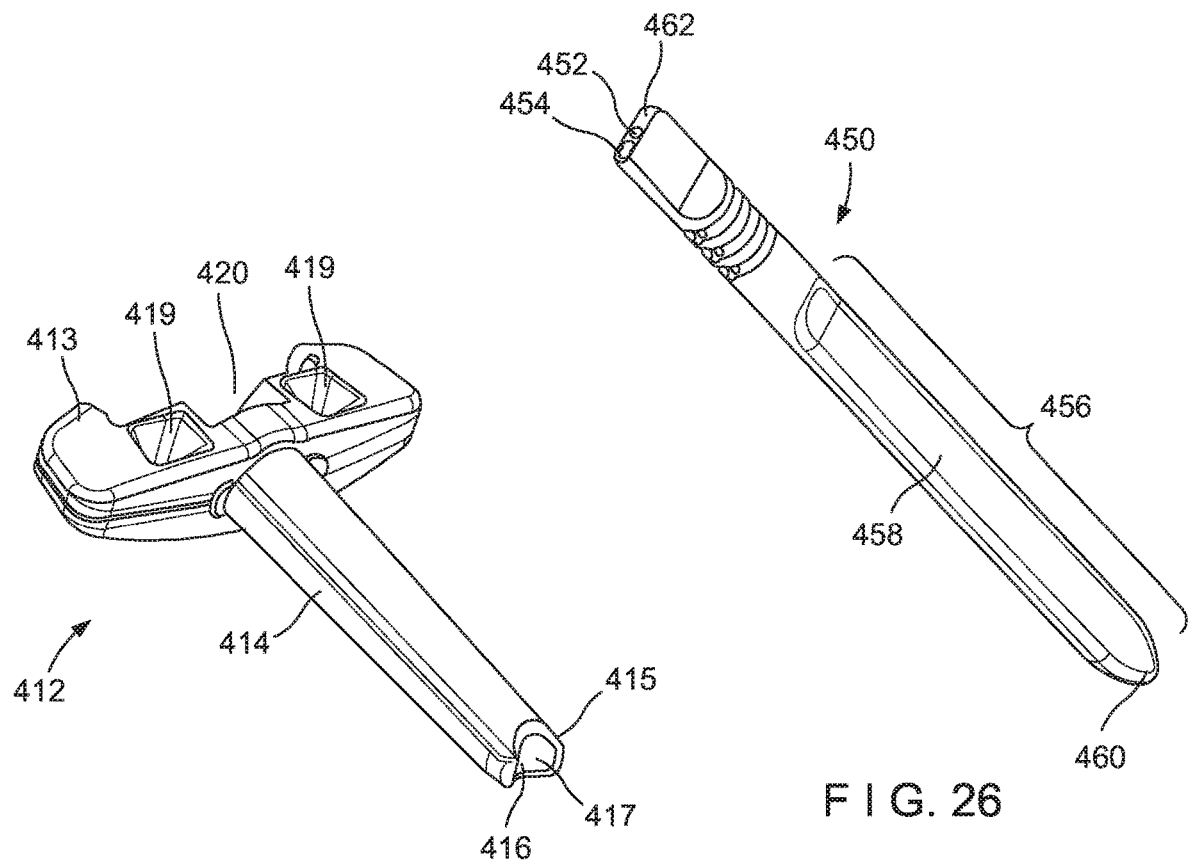
FIG. 24
FIG. 26
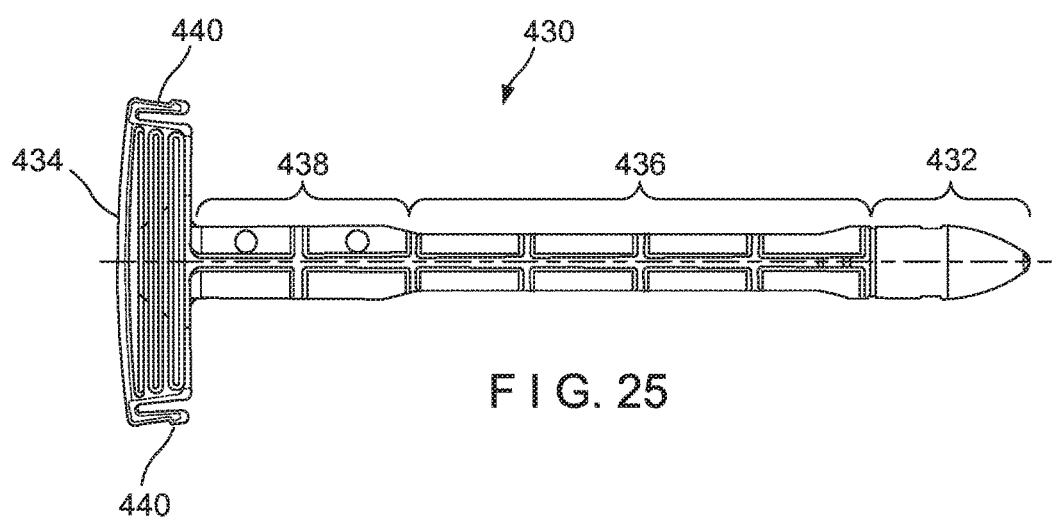
FIG. 25

DEVICE AND SYSTEM FOR FACILITATING INSERTION OF A BONE TREATMENT DEVICE

FIELD OF THE INVENTION

The present disclosure relates generally to a device and a system facilitating the insertion of a bone treatment device into a living body and, in particular, devices and systems for facilitating the insertion of an intramedullary nails into a bone (e.g., a tibia).

BACKGROUND

Procedures for the insertion of intramedullary (IM) nails into the tibia could be performed with a suprapatellar approach. While this technique often facilitates the treatment of proximal and distal fractures of the tibia, elevated pressure may be applied to the knee joint during the drilling and reaming of the entry path for the IM nail as well as during insertion of the nail itself.

SUMMARY OF THE INVENTION

The present disclosure relates to a device for facilitating the insertion into a living body of a bone treatment device includes an outer sleeve of flexible material forming an outer conduit extending longitudinally therethrough for the insertion of the bone treatment device to target sites within the body. A distal opening of the outer conduit is open so that, when the outer sleeve is in a desired position within the body the bone treatment device inserted through the outer conduit exits the outer sleeve adjacent to a target portion of bone.

The device also includes an inner sleeve received within the outer sleeve and defining an inner conduit within the outer conduit. The inner sleeve forms a protective covering within the outer conduit. The inner sleeve is formed of metal. The inner sleeve is split longitudinally. Portions of the inner sleeve on opposite sides of the split are coupled to one another so that the diameter of the inner conduit is adjustable within a predetermined range in response to forces exerted thereon by one of the bone treatment device and tissues surrounding the outer sleeve.

The present embodiments further relate to a system treating a bone including an insertion device configured for insertion within a living body, the insertion device providing a conduit to a target site within the body. The insertion device includes an outer sleeve of flexible material forming an outer lumen extending longitudinally therethrough. A distal opening of the outer lumen being open so that, when the outer sleeve is in a desired position within the body a bone treatment device inserted through the outer lumen exits the outer sleeve adjacent to a target portion of bone and an inner sleeve received within the outer sleeve and defining an inner lumen within the outer lumen. The inner sleeve forms a protective covering within the outer lumen. The inner sleeve is formed of metal. The inner sleeve being split longitudinally. Portions of the inner sleeve on opposite sides of the split are coupled to one another so that a diameter of the inner lumen is adjustable within a predetermined range in response to forces exerted thereon by one of items inserted through the conduit and tissues surrounding the outer sleeve.

The system also includes a wire guide sized and shaped for insertion through the conduit to the target site. The wire guide includes a first lumen extending along a central longitudinal axis of the wire guide. The first lumen is sized and shaped to slidably receive a guide wire therethrough. The wire guide includes a second lumen laterally offset from and parallel to the first lumen. The second lumen is sized and shaped to slidably receive a guide wire therethrough.

BRIEF DESCRIPTION OF THE DRAWINGS

FIG. 19 shows a perspective view of a sheet of material from which the core protection sleeve of FIG. 18 may be formed;

FIG. 20 shows two sheets of FIG. 19 positioned to be joined to form the core protection sleeve of FIG. 18;

FIG. 21 shows a side view of an inner protection sleeve according to a further embodiment;

FIG. 24 shows a perspective view of a protection assembly according to a further embodiment;

FIG. 25 shows a side view of a trocar according to an embodiment;

FIG. 26 shows a perspective view of a wire guide according to a further embodiment;

DETAILED DESCRIPTION

Figure 1:
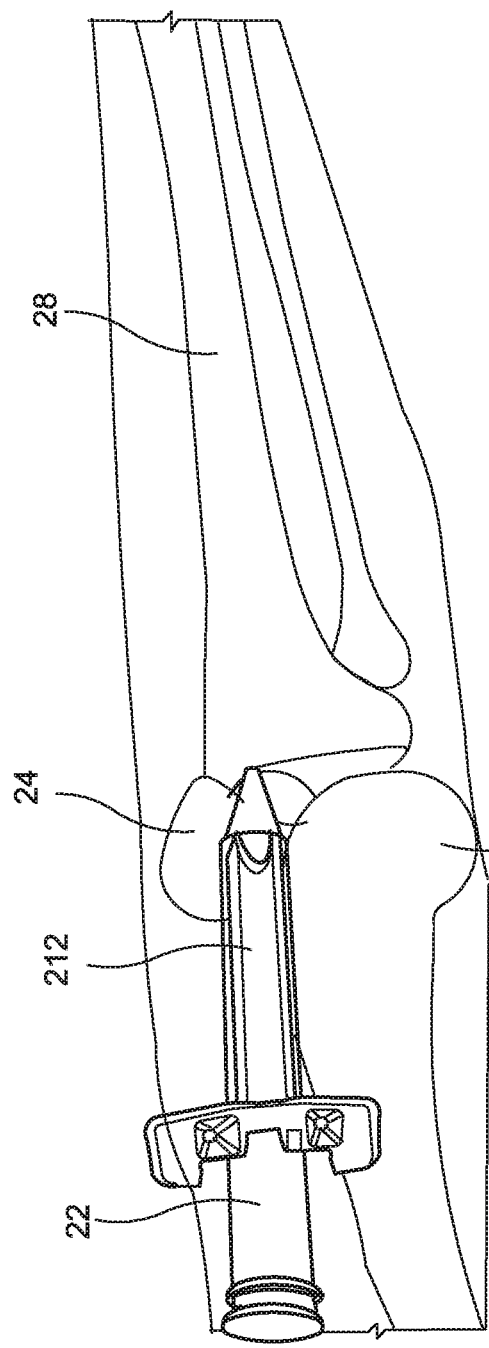
FIG. 1 shows a perspective view of an apparatus according to an embodiment in position adjacent to and within a leg.

The present disclosure may be further understood with reference to the following description and the appended drawings, wherein like elements are referred to with the same reference numerals. Exemplary embodiments describe devices and procedures for suprapatellar insertion of tibial IM nails. As used herein, the terms distal and proximal refer to a direction away from a point of attachment of the leg to the body (distal) and toward the point at which the leg is attached to the body (proximal). Although the embodiments described herein a specifically configured for the procedures for suprapatellar insertion of tibial IM nails, those skilled in the art will understand that the embodiments described herein may also be employed for procedures involving spine surgeries.

As would be understood by those skilled in the art, fractures of the tibia may be treated by the insertion of an IM nail and, in certain cases, the IM nail is inserted with a suprapatellar approach. In these cases, instrumentation such as drills and reamers as well as the IM nail itself are inserted into the proximal end of the tibia via a space between the patella and the femur. This approach requires displacement of the patella and may place pressure on the patella, its supporting anatomy and the surrounding tissue. Generally, a protection sleeve is inserted through this space to protect the surrounding tissue from damage that might otherwise result were this instrumentation or the nail itself to contact surrounding tissue. The tissue surrounding this space is displaced and subjected to significant stress for the entire time that the protection sleeve remains in this position. The present embodiments provide for the protection of surrounding tissue while reducing the stress placed on this tissue during the procedure. In general, such procedures involve reducing the fracture (using any known techniques), after which a length and diameter of the IM nail are determined also using any known technique. After this, an incision is made and an entry site for the IM nail is determined. In addition, techniques such as blunt dissection may be employed to loosen the patella and allow it to be moved away from the femur.

Figure 2:
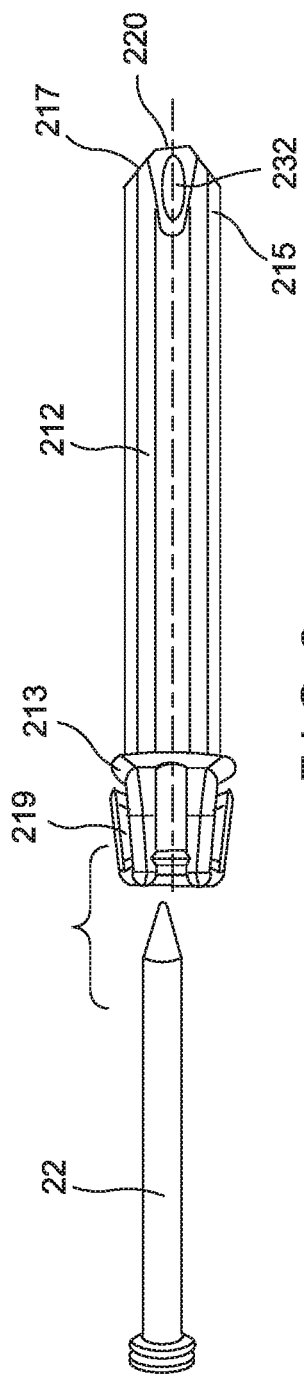
FIG. 2 shows an exploded view of the apparatus of FIG. 1.

As seen in FIGS. 1 and 2, a protection sleeve assembly 212 described in detail below in regard to FIG. 13 may be employed. A trocar 22 is then inserted through the protection sleeve assembly 212 and the combination is inserted to the entry site for the IM nail entering the body via the incision and passing through the knee joint, for example, between the articular surface of the patella 24 and the distal femur 26 to the proximal end of the tibia 28. The protection sleeve assembly 212 is then fixed in place through the placement of guide wires into either the tibia or the femur as will be described in more detail below.

Figure 38:
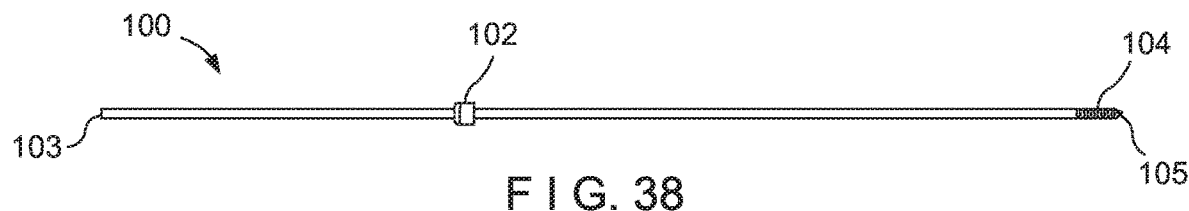
FIG. 38 shows a perspective view of a fixation guide wire according to an embodiment.
Figure 39:
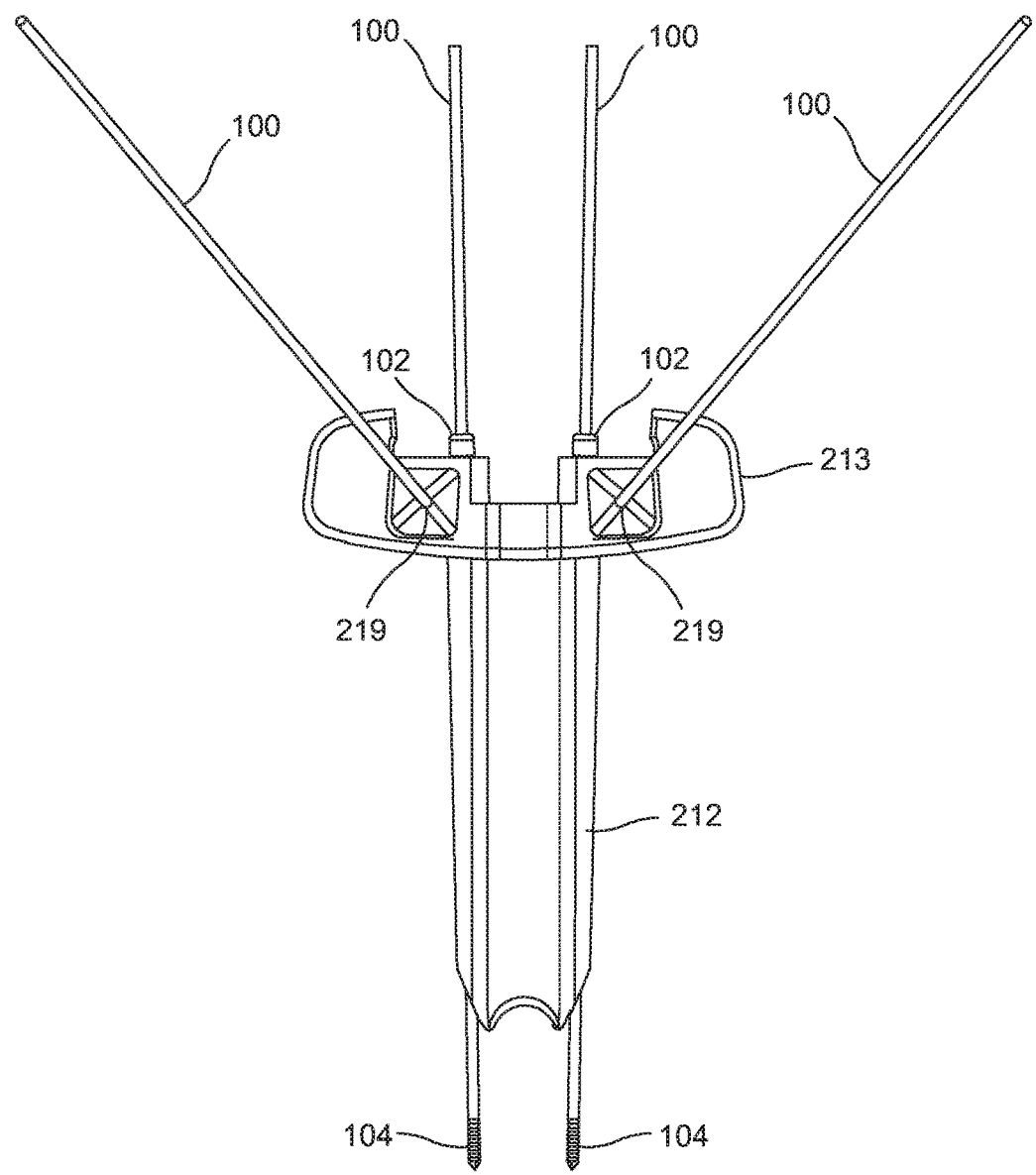
FIG. 39 shows a top view of the protection assembly of FIG. 13 with the fixation guide wires of FIG. 38.
Figure 40:
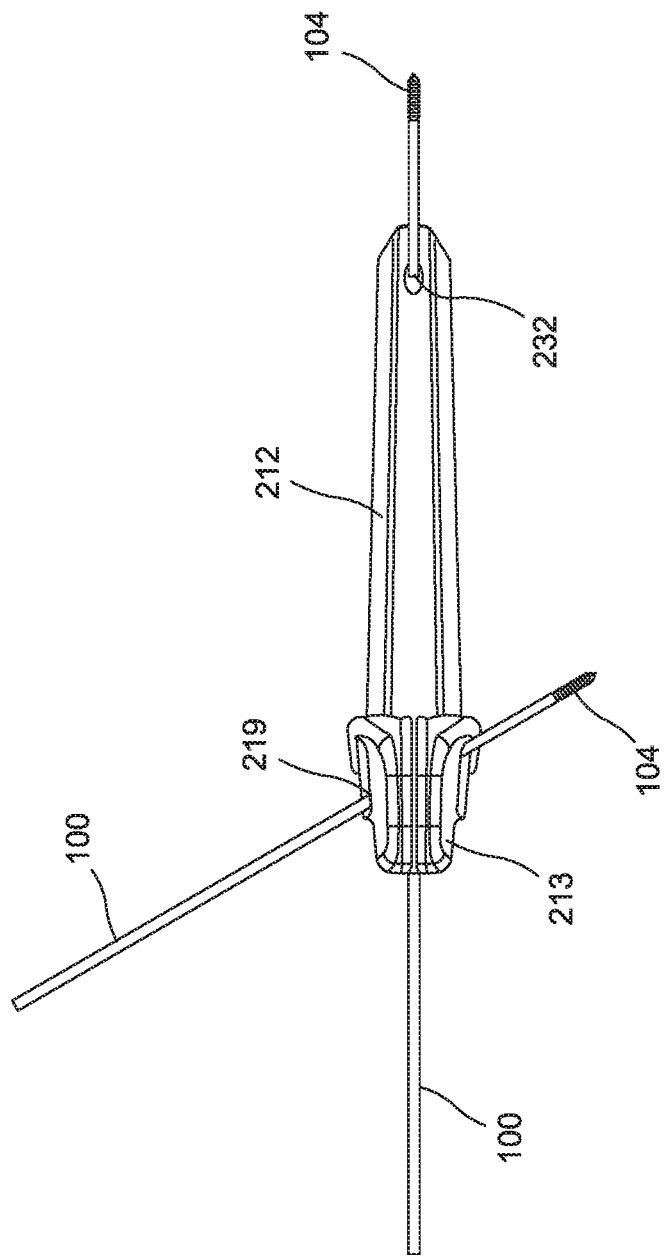
FIG. 40 shows a side view of the protection assembly of FIG. 13 with the fixation guide wires of FIG. 38.

As seen in FIGS. 38-40, tibial fixation may be performed using a fixation guide wire 100. The fixation guide wire 100 extends from a proximal end 103 to a distal end 105 and includes a shoulder or a stop 102, for example welded to the fixation guide wire 100, and a threaded tip 104 at the distal end 105. The stop 102 is sized and shaped to prevent the fixation guide wire 100 from passing into the protection sleeve assembly 212 beyond a desired depth. The stop 102 is positioned so that, when the fixation guide wire 100 is inserted into the tibia as desired, contact between the stop 102 and the protection assembly sleeve 212 holds the protection sleeve assembly 212 against the tibia in a desired position.

As will be described below, the protection sleeve assembly 212 includes an inner sleeve formed of metal, such as stainless steel and an outer sleeve is formed of a yielding material such as, for example, a flexible plastic. Thus, the inner metal sleeve protects the outer plastic sleeve from damage that might otherwise occur to the softer plastic material during drilling, reaming, etc. The apparatus is inserted until the trocar 22 reaches the surface of the tibia 28 at the entry site—e.g., the anterior surface of the proximal tibia.

Figure 3:
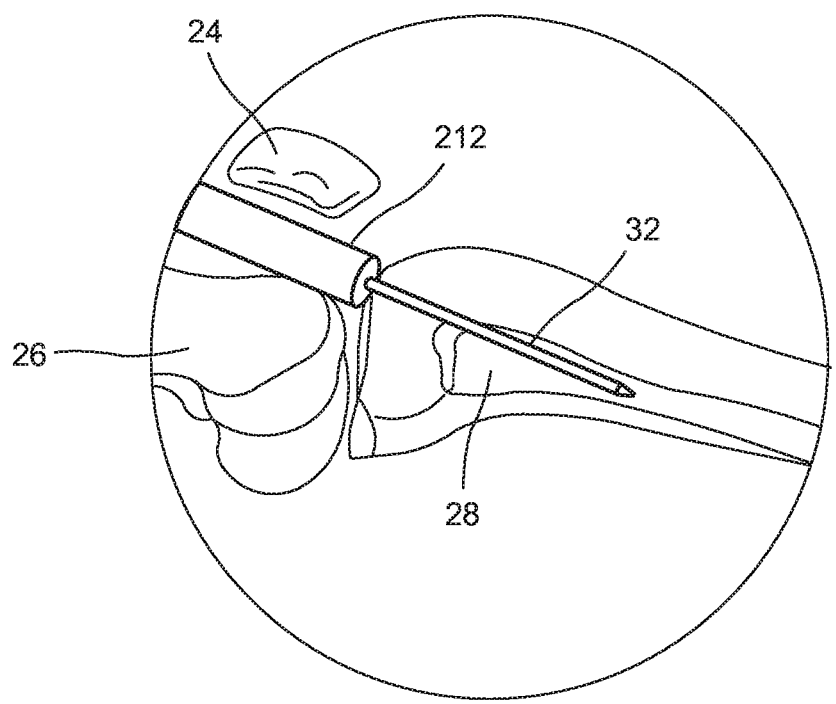
FIG. 3 shows a view of the anatomy of the knee joint and the apparatus of FIG. 1 along with a guide wire that has been inserted into a tibia.
Figure 4:
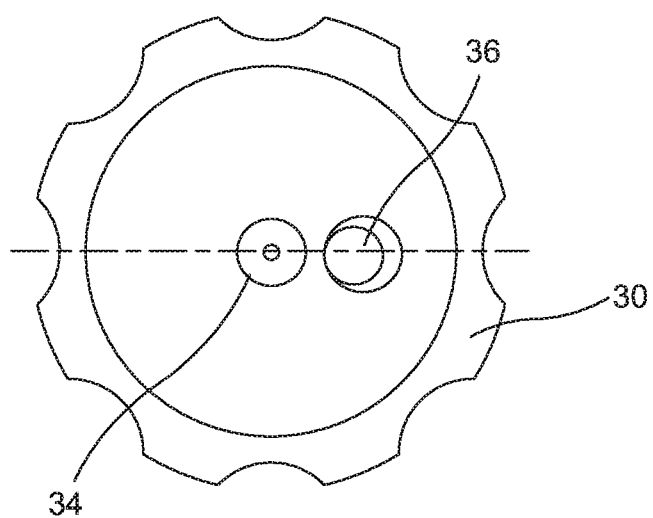
FIG. 4 shows a view of a proximal end of a wire guide for use with the apparatus of FIG. 1.

At this point, the trocar 22 is removed and, as shown in FIGS. 3 and 4, a wire guide 30 is inserted through the protection sleeve assembly 212 to guide the placement of a first guide wire 32 through the entry site along the desired path that will be drilled out for the insertion of the IM nail into the medullary canal of the tibia 28. Those skilled in the art will understand that the guide wire 32 may be inserted as desired using any known techniques. In this case, the guide wire 32 is placed into the tibia 28 via a wire guide 30 which is inserted through the protection sleeve assembly 212 to the entry site. The guide wire 32 is passed through a central lumen 34 that extends along a longitudinal axis of the wire guide 30 (coincident, in this embodiment, with a central axis of the protection sleeve assembly 212) to enter the tibia 28 along a path parallel to and defined by a path of the central lumen 34 of the wire guide 30. The positioning of the guide wire 32 may then be checked and adjusted using the wire guide 30 as follows.

Figure 5:
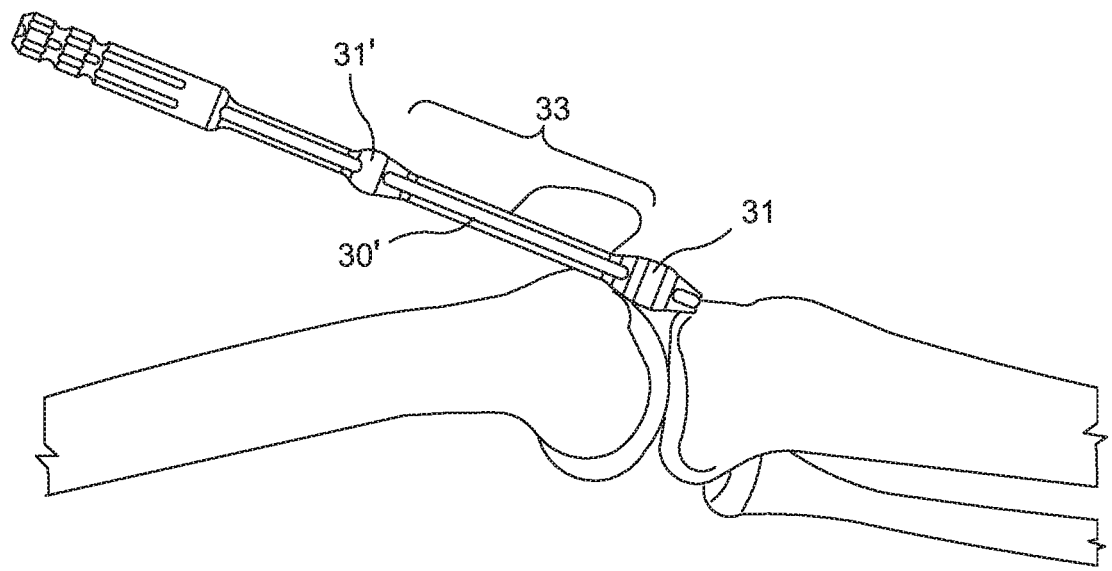
FIG. 5 shows a perspective view of a wire guide according to a further embodiment including increased and reduced diameter portions.

After the position of the guide wire 32 has been checked, if it is determined that the position of the guide wire 32 should be adjusted, the physician removes the wire guide 30 by withdrawing it over the guide wire 32 until the guide wire 32 exits the wire guide 30 and then re-inserts the guide wire 32 into an offset lumen 36 that is radially offset from and parallel to the central lumen 34. The wire guide 30 is then passed over the guide wire 32 through the protection sleeve assembly 212 to the proximal surface of the tibia and rotated as desired until the central lumen 34 is aligned with a desired path along which it is desired to insert a second guide wire 32 into the tibia 28. The second guide wire 32 is then placed as desired and the first guide wire 32 is removed. In addition, as shown in FIG. 5 the outer diameter of a wire guide 30' according to a further embodiment varies along its length to allow for partial radial collapse of the protection sleeve assembly 212 when the wire guide 30' is received therethrough. Specifically, an outer diameter of the wire guide 30' includes a distal portion 31 whose outer diameter substantially correspond to an inner diameter of the protection sleeve assembly 212 at a distal end thereof which, when the wire guide 30' is fully inserted, contacts the tibia and a proximal portion 31' which, when the wire guide 30' is fully inserted is received in a proximal end of the protection sleeve assembly 212 separated by a central reduced diameter portion 33.

Figure 6:
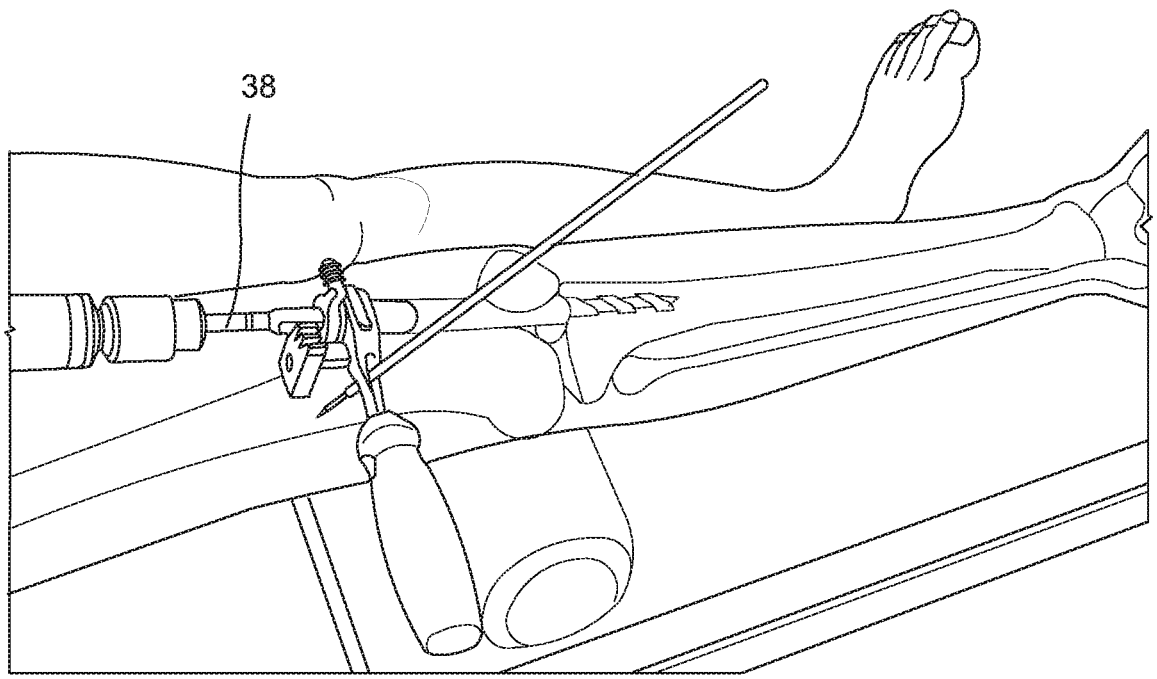
FIG. 6 shows a perspective view of the assembly of FIG. 1 in use in conjunction with a drill bit.

This ensures that the wire guide 30' is properly centered in the protection sleeve assembly 212 while allowing the middle portion of the protection sleeve assembly 212 to partially collapse radially, reducing pressure applied to the surrounding tissue as will be described in more detail below. As shown in FIG. 6, a drill bit 38 is then advanced over the guide wire 32 (the second guide wire) and advanced through the protection sleeve assembly 212 to the entry site at which point the physician drills an entry hole to the medullary canal as would be understood by those skilled in the art. Thereafter, the physician removes the drill bit and may, if desired, advance a reamer over the guide wire 32 (or a reaming rod i.e., a 2.5-3 mm long flexible steel rod) to ream the drilled opening and or the medullary canal as would be understood by those skilled in the art.

Figure 7:
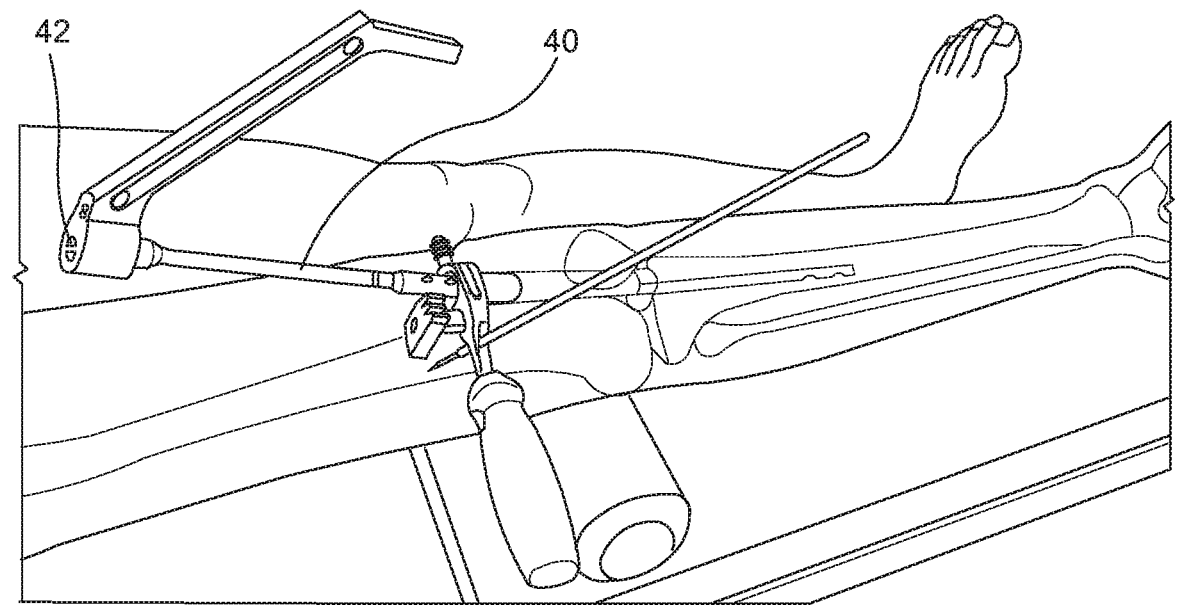
FIG. 7 shows a perspective view of an IM nail being inserted into a tibia in conjunction with the apparatus of FIG. 1.
Figure 8:
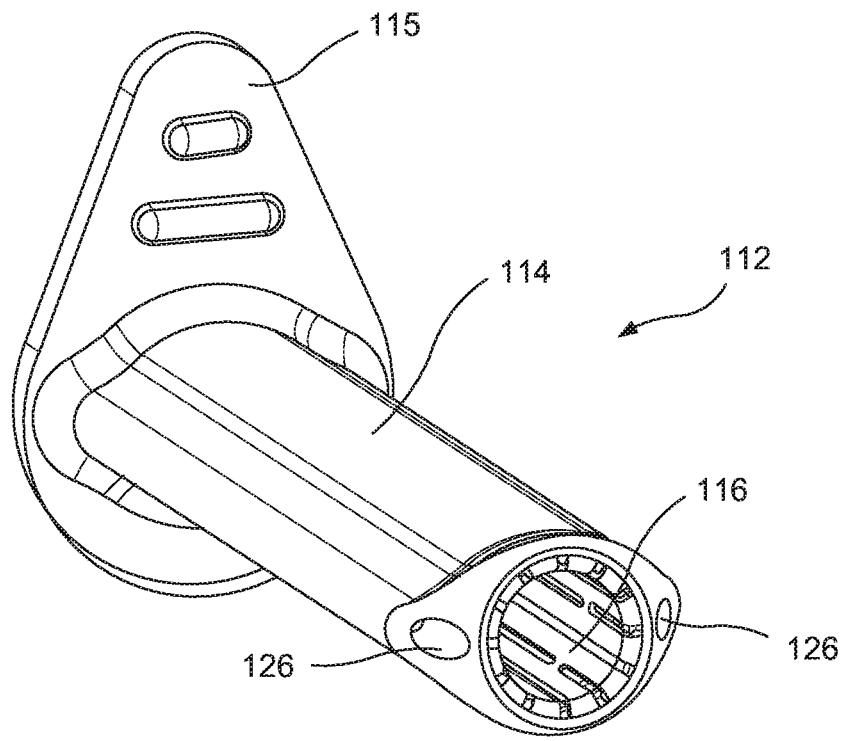
FIG. 8 shows a perspective view of a protection assembly according to a further embodiment.
Figure 9:
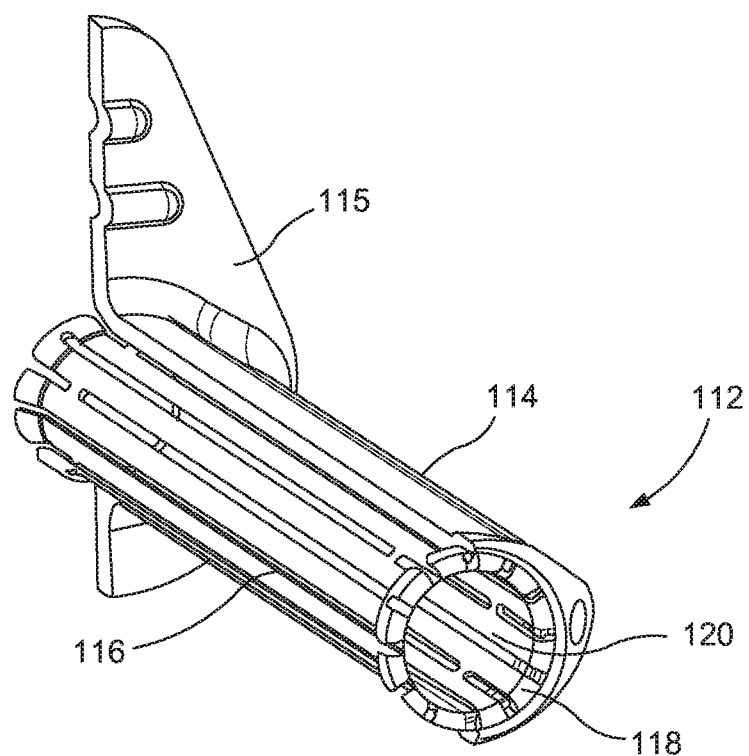
FIG. 9 shows a partially cross-sectional view of the assembly of FIG. 8.
Figure 10:
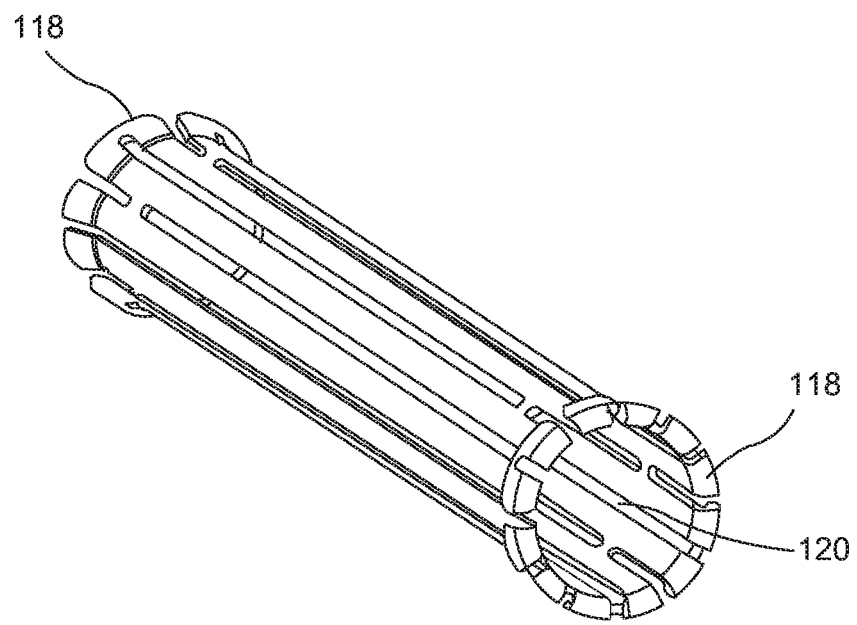
FIG. 10 shows a view of a core protection sleeve of the assembly of FIG. 8.

As shown in FIG. 7, once the entry path and the medullary canal have been prepared, the reamer may be removed and the IM nail 40 is prepared for insertion. As would be understood by those skilled in the art, a proximal end of the IM nail 40 may be coupled to an insertion handle 42 and the distal end of the IM nail 40 is inserted through the protection sleeve assembly 212 to the entry path. During a time between the completion of the preparation of the entry path/medullary canal and the time when the IM nail 40 is ready for insertion, the protection sleeve assembly 212 partially collapses radially inward permitting the surrounding tissue to relax a bit reducing trauma associated with its displacement. This again reduces the time during which the tissue of the suprapatellar space is subjected to the high levels of stress. The IM nail 40 may then be inserted into the tibia 28 and locked in place using any known techniques.

As shown in FIGS. 8-12, a further embodiment of a protection sleeve assembly 112 for use in the insertion of an IM nail 40 via, for example, a suprapatellar approach is usable with a separate handle. Specifically, the sleeve 112 includes an outer soft protection sleeve 114 extending from a proximal base 115 that couples to a handle in a known manner. The outer sleeve 114 surrounds a metal inner core sleeve 116 that protects the outer sleeve 114 from being damaged by drills reamers, etc. inserted through the assembly 112. The core sleeve 116 includes radial flanges 118 that mate with corresponding structures of the outer sleeve 114 to maintain the core sleeve 116 at a desired position within the outer sleeve 114.

In addition, the radial flanges 118 make the proximal and distal ends of the core sleeve 116 substantially incompressible making it easier to draw items that have been inserted distally beyond the assembly 112 back into the assembly 112 by ensuring that the diameter of the distal end of the core sleeve 116 remains sufficient to receive the item. The core sleeve 116 is structured to permit the core sleeve 116 to deflect radially inward when subject to compressive forces (e.g., forces applied by surrounding tissue) when a lumen 120 thereof is not occupied by an incompressible item (e.g., an IM nail, a drill, a reamer, etc.).

Figure 11:
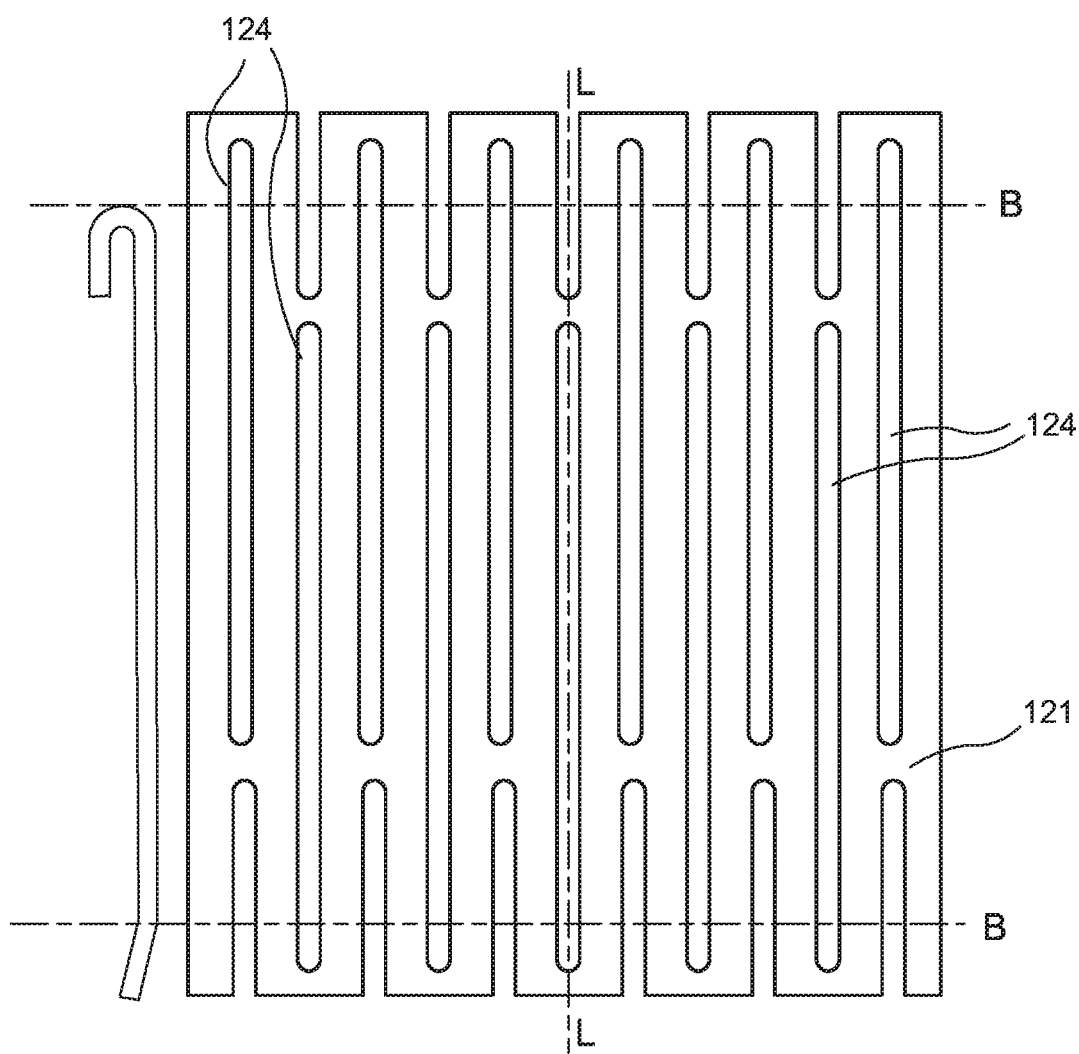
FIG. 11 shows a perspective view of a sheet of material from which the core protection sleeve of FIG. 10 may be formed.
Figure 12:
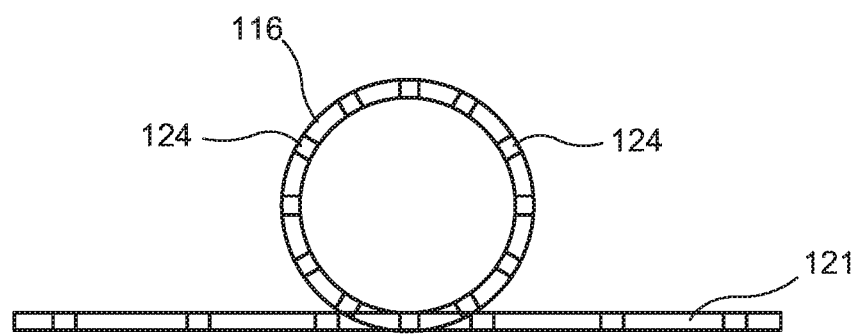
FIG. 12 shows an end view of the sheet of FIG. 11 and the core protection sleeve of FIG. 10.

As shown in FIGS. 11 and 12 the core sleeve 116 of this embodiment may be formed from a sheet 121 of metal. The sheets may be formed from any suitable material such as any hardened spring steel wrapped around a longitudinal axis L to form a cylinder and bent over bending axes B to form the radial flanges 118. The sheet 121 includes a series of longitudinal voids 124 that enhance the flexibility of the core sleeve 116 so that, when no instrument is passed through the sleeve assembly 112 (or when an outer diameter of an item received within the assembly 112 is less than an inner diameter of the core sleeve 116), the assembly 112 collapses radially inward to reduce trauma to the tissue surrounding the assembly 112. In addition, the outer sleeve 114 of this embodiment includes 2 guide wire lumens 126 extending on opposite sides of the lumen 120. Although in this embodiment the guide wire lumens 126 extend parallel to the lumen 120, the guide wire lumens 126 may extend in different directions relative to the lumen 120. As would be understood by those skilled in the art, the guide wire lumens 126 may be used to fix the assembly 112 in a desired position on the tibia by inserting guide wires therethrough into the proximal end of the tibia. In another embodiment, the core sleeve 116 may be formed from a tube of the any suitable material, the tube having longitudinal voids similar to the longitudinal voids 124.

Figure 13:
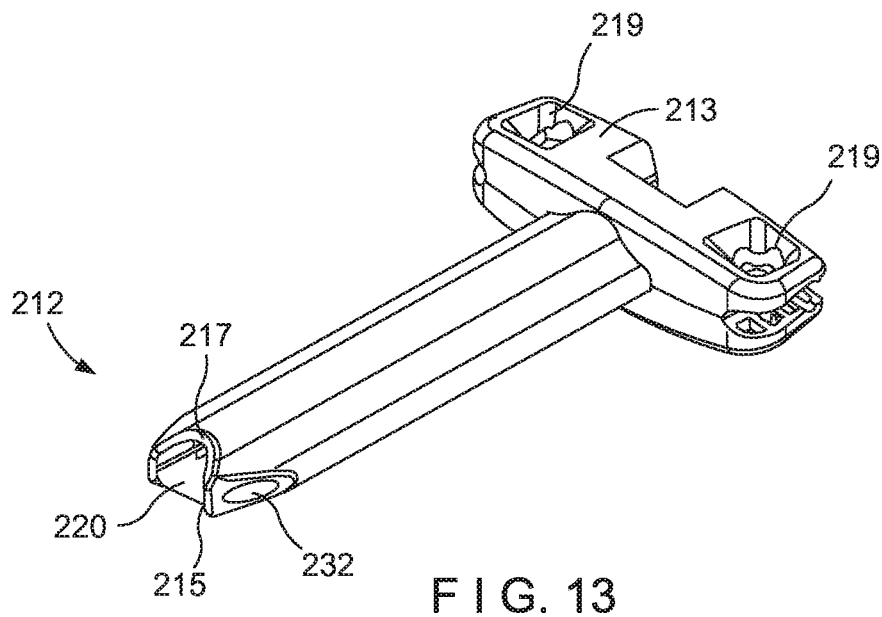
FIG. 13 shows a perspective view of a protection assembly according to yet a further embodiment.
Figure 14:
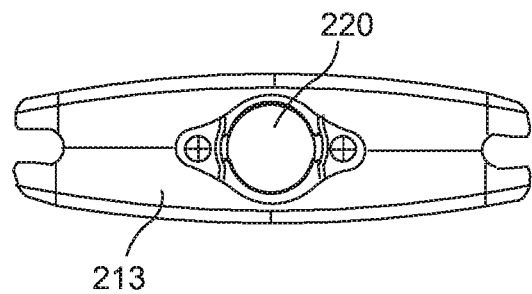
FIG. 14 shows an end view of the protection assembly of FIG. 13.
Figure 15:
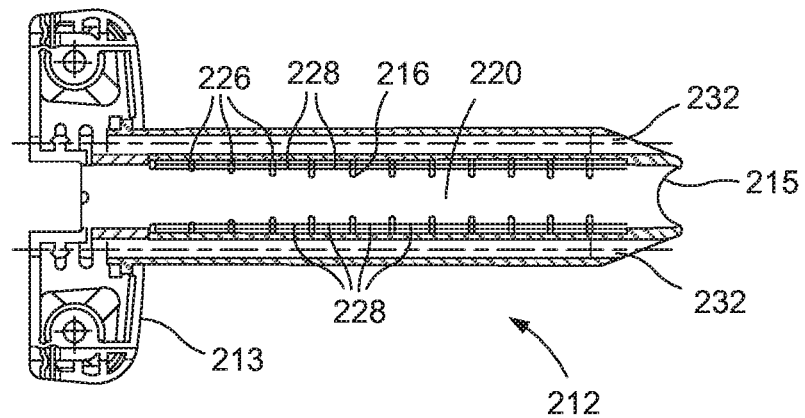
FIG. 15 shows a cross-sectional view of the protection assembly of FIG. 13.

FIGS. 13-15 show a protection sleeve assembly 212 according to yet another embodiment that extends from a handle 213 at a proximal end thereof to a distal end 215 shaped to rest substantially flush against a target portion of bone. The outer sleeve 214 surrounds a metal inner core sleeve 216 that protects the outer sleeve 214 from being damaged by drills reamers, etc. inserted through the assembly 212. The distal end 215 is preferably made more rigid than the rest of the device so that it remains fully open and the distal end 215 includes a chamfer 217 to facilitate drawing items (e.g., a reamer) that have been inserted distally beyond the assembly 212 back into the assembly 212 by ensuring that the diameter of the distal end of the assembly 212 remains sufficient to receive the item. The core sleeve 216 is structured to permit the core sleeve 216 to deflect radially inward when subject to compressive forces (e.g., forces applied by surrounding tissue) when a lumen 220 thereof is not occupied by an incompressible item (e.g., an IM nail, a drill, a reamer, etc.).

As seen in FIG. 13, the handle 213 also includes two guide wire insertion openings 219 configured to permit the insertion of guide wires into the femur to fix the assembly 212 to the femur if that is desired as an alternative to or in addition to fixation of the assembly 212 to the tibia. The openings 219 are formed as a substantially conical opening to permit the guide wires to be angulated relative to the handle 213 at any desired orientation within a permitted range of angulation. For example, the openings 219 may permit the insertion of a guide at any angle within a cone having an apex angle of 55 degrees.

Figure 16:
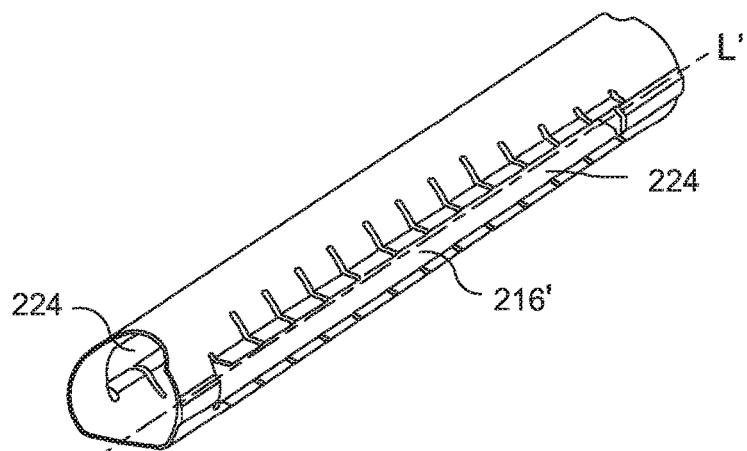
FIG. 16 shows an inner protection sleeve of an embodiment of the assembly of FIG. 13.
Figure 17:
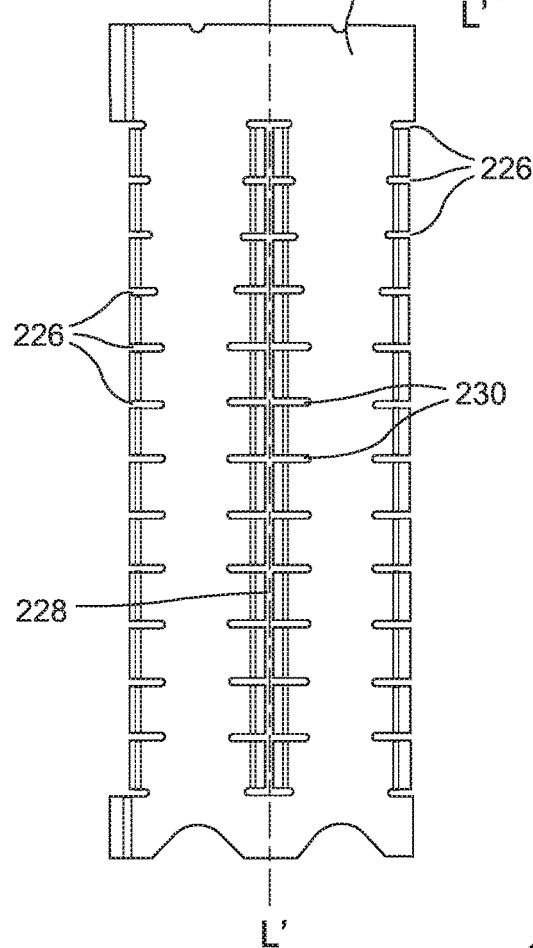
FIG. 17 shows a perspective view of a sheet of material from which the core protection sleeve of FIG. 16 may be formed.

As shown in FIGS. 16-20, the core sleeve 216 of this embodiment may be formed from one or more sheets 222 of a metal or other material similar to that described above in regard to the core sleeve 116. As seen in FIGS. 16 and 17, a core sleeve 216' is formed by wrapping a single sheet 222' around a longitudinal axis L' to form a generally ovoid structure with longitudinal openings 224 on opposing sides thereof. The ends of the wrapped sheet 222' may then be welded to form the ovoid tube-like structure.

As seen in FIG. 17, the sheet 222 includes a series of transverse slits 226 on outer edges thereof. The longitudinal openings 224, formed as slots on opposite sides of the core sleeve 216', are formed by bending radially outward fins 228 formed between adjacent ones of the slits 226. The resulting structure of the core sleeve 216' fits into a correspondingly shaped interior space of the outer sleeve 214 as shown in FIG. 15. In another embodiment, the longitudinal openings 224 may be shaped along any curve, e.g., a helix curve. In another embodiment, the core sleeve 216 may be formed from a tube of a material to that described above in regard to the core sleeve 116, the tube having longitudinal openings similar to the longitudinal voids 224 and transverse slits similar to the transverse slits 226.

The sheet 222' also includes a longitudinal slit 228 with a series of transverse slits 230 intersecting the slit 228 at regular intervals. The core sleeve 216 is shaped and structured to enhance the compressibility of the assembly 212 in direction transverse to the axis L and particularly in a direction across the width of the slots 224. The assembly 212 is constructed to have maximum deflectability in a direction from which the maximum compressive force is applied by the surrounding tissue. That is, for this device, the assembly 212 is designed to compress more easily in an anterior to posterior direction as this is the direction of maximum force applied to the assembly 212 by the surrounding tissue.

As would be understood by those skilled in the art, a width of the longitudinal openings 224 (an extent of the openings 224 in a direction transverse to the longitudinal axis of the assembly 212) defines a maximum deflection of the core sleeve 216 and, consequently of the assembly 212. That is, when deflected to a maximum amount the opposite sides of the longitudinal openings 224 will contact one another. As described above, when no instrument is passed through the sleeve assembly 212 (or when an outer diameter of an item received within the assembly 212 is less than an inner diameter of the core sleeve 216), the assembly 212 collapses radially inward to reduce trauma to the tissue surrounding the assembly 212. In addition, the outer sleeve 214 of this embodiment includes 2 guide wire lumens 232 extending parallel to and on opposite sides of the lumen 220.

Figure 18:
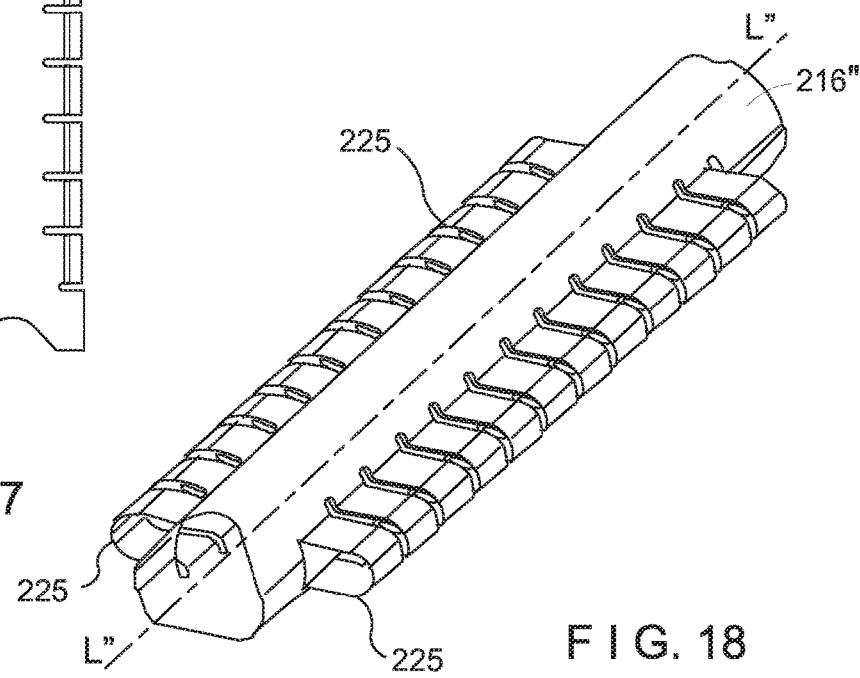
FIG. 18 shows an inner protection sleeve of a further embodiment of the assembly of FIG. 13.

As seen in FIGS. 18-20, an inner core protection sleeve 216" may be formed from two sheets 222" each of which is pressed into a substantially symmetrical shape and welded together at edges of the sheets. In contrast to the sleeve 216', the sleeve 216" does not include lateral slots 224. Rather the fins 226' of the sheet 222" are bent to extend laterally away from a central axis L" of the sleeve 216" so that, as a group, they form wings 225 on either side of the sleeve 216". Similarly to the openings 224, the width of the wings 225 defines the maximum deflection of the core sleeve 216" and, consequently, of an assembly within which it is mounted. That is, when deflected to a maximum amount the opposite sides of the wings 225 contact one another.

Figure 22:
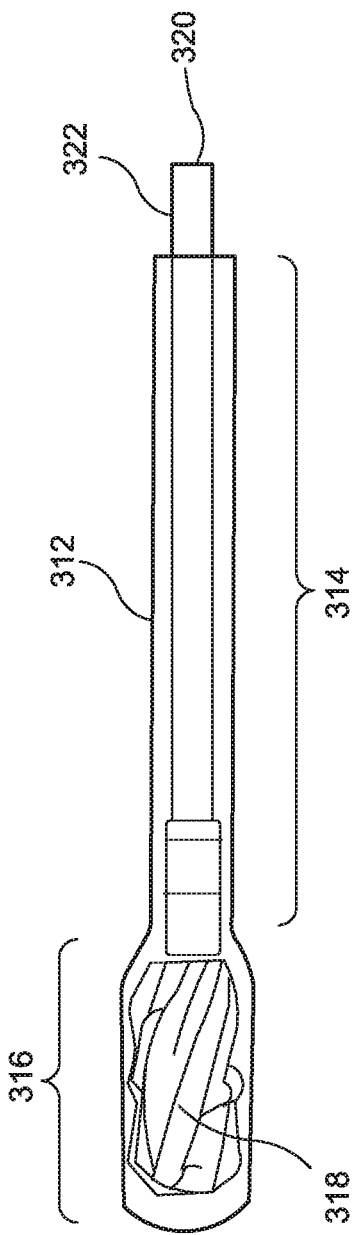
FIG. 22 shows a cross-sectional view of the inner protection sleeve of FIG. 21.
Figure 23:
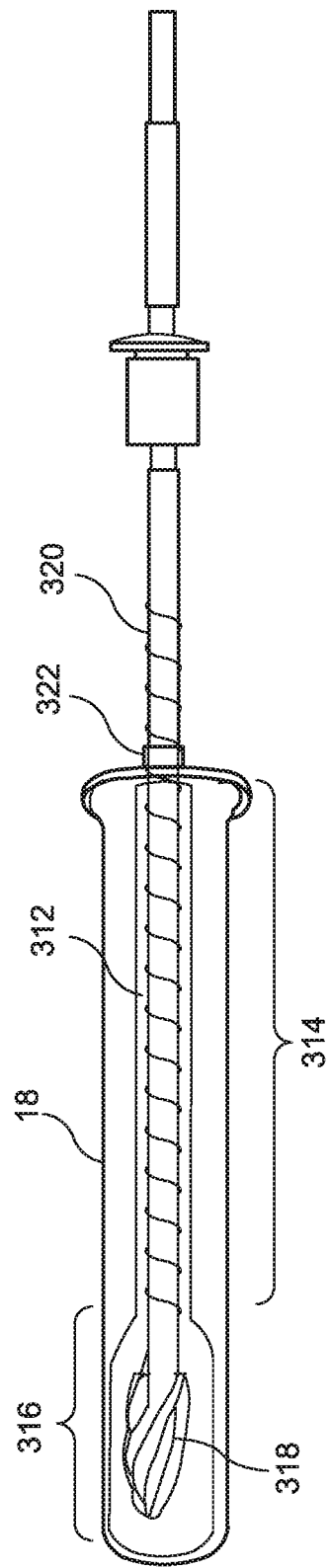
FIG. 23 shows a cross-sectional view of the inner protection sleeve of FIG. 21 received within an outer sleeve.
Figure 27:
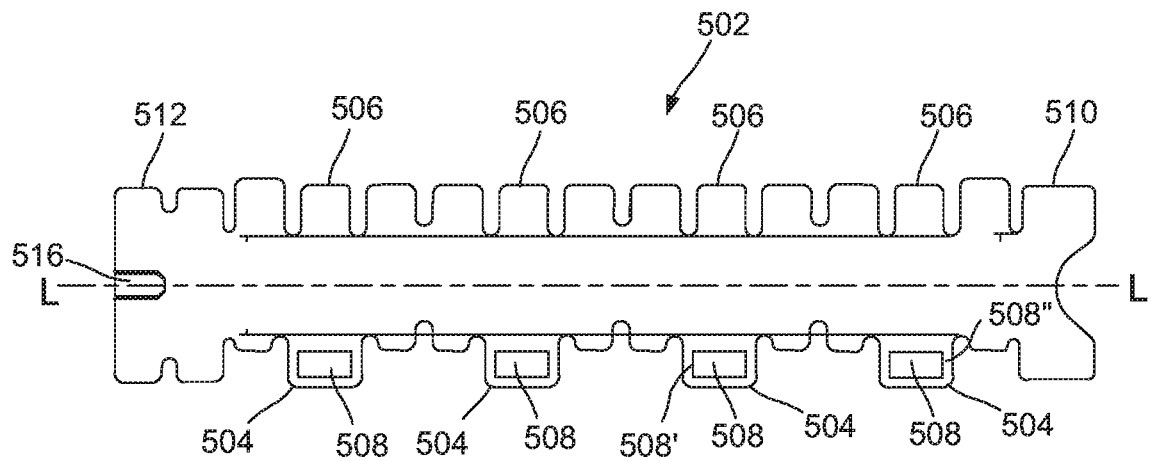
FIG. 27 shows a side view of a sheet of material from which the core protection sleeve of FIGS. 30-32 may be formed.

A core protection sleeve 312 for inclusion in any of the protection sleeve assemblies described herein is shown in FIGS. 21-23. The sleeve 312 is configured to be inserted into any of the outer sleeves described in this application to form a durable protection sleeve assembly which will resist damage during drilling and reaming, etc. In this embodiment, the core protection sleeve 312 includes a proximal portion 314 having a first diameter and a distal portion 316 having a second diameter greater than the first diameter. The increased diameter distal portion 316 is sized to center the sleeve 312 at the distal end of the protection sleeve assembly to properly aim the operational head 318 of a reamer or drill bit 320 while the reduced diameter proximal portion 314 is sized to receive a drive shaft 322 of the reamer or drill bit 320 with clearance allowing the protection sleeve assembly to partially collapse.

As would be understood by those skilled in the art, inner diameters of the proximal and distal portions 314 and 316, respectively, are sized to allow sufficient clearance to the parts of the reamer or drill bit 320 housed therein so that the reamer or drill bit 320 may rotate freely within the core protection sleeve 312. Thus, only a portion of the protection sleeve 312 that houses the distal portion 316 of the core protection sleeve 312 is prevented from radially collapsing to reduce tissue stress. Thus, when the core protection sleeve 312 is in use, a large portion of the length of the protection sleeve 312 is free to compress and reduce the stress on surrounding tissue. As shown in FIG. 23 the clearance between the outer diameter of the proximal portion 316 extends from the proximal end of the distal portion 314 to the proximal end of the protection sleeve 312 allowing for partial radial collapse of the protection sleeve 312 along this entire portion. As would be understood, the core protection sleeve 312 may be used only with devices having a reduced diameter shaft extending along a significant portion of its length.

As shown in FIG. 24, a protection sleeve assembly 412 according to a further embodiment is substantially similar to the protection sleeve assembly 212 described above except that the assembly 412 does not include any guide wire lumens and thereby affords a reduced profile further reducing trauma to surrounding tissue. That is, the protection sleeve assembly 412 may be selected by a user who does not want to insert guide wires into the tibia to fix the assembly 412 in the desired position. In this case, the assembly 412 would be fixed only via guide wires inserted through the guide wire openings 419 in the handle 413. As seen in FIG. 24, the protection sleeve assembly 412 extends from a handle 413 at a proximal end thereof to a distal end 415 shaped to rest substantially flush against a target portion of bone.

The outer sleeve 414 surrounds a metal inner core sleeve 416 that protects the outer sleeve 414 from being damaged by drills reamers, etc. inserted through the assembly 412. The core sleeve 416 may be constructed in accord with any of the embodiments described herein. The distal end 415 is preferably made more rigid than the rest of the device so that it remains fully open and the distal end 415 includes a chamfer 417 to facilitate drawing items (e.g., a reamer) that have been inserted distally beyond the assembly 412 back into the assembly 412 by ensuring that the diameter of the distal end of the assembly 412 remains sufficient to receive the item.

As indicated above, the core sleeve 416 is structured to permit the core sleeve 416 to deflect radially inward when subject to compressive forces (e.g., forces applied by surrounding tissue) when a lumen thereof is not occupied by an incompressible item (e.g., an IM nail, a drill, a reamer, etc.). The handle 413 also includes two guide wire insertion openings 419 configured to permit the insertion of guide wires into the femur to fix the assembly 412 to the femur. The openings 419 are formed as a substantially conical opening to permit the guide wires to be angulated relative to the handle 413 at any desired orientation within a permitted range of angulation.

FIG. 25 shows a trocar 430 for use with any of the protection sleeve assemblies described herein. The trocar 430 includes a blunt, tapered distal tip 432. The trocar 430 is sized so that, when a handle 434 at the proximal end thereof is seated in a correspondingly sized and shaped recess of a handle of a protection sleeve assembly (e.g., within recess 420 of the handle 413 of the assembly 412), the distal tip 432 projects distally from the sleeve 414 to provide a blunt dissection tip facilitating the insertion of the combined trocar 430 and assembly 412 over a guide wire to a target side adjacent to the proximal end of the tibia.

The trocar 430 includes a reduced diameter proximal shaft 436 having a diameter smaller than that of the distal tip 432. The diameter of the distal tip 432 and of a proximal portion 438 of this embodiment substantially corresponds to an inner diameter of the core sleeve 416 to center the trocar 430 within the assembly 412. The trocar 430 also includes optional locking structures 440 configured to snap into engagement with corresponding structures in the recess 420 to hold the trocar 430 in a desired position within the assembly 412. As would be understood by those skilled in the art, a wire guide such as the wire guide 30 may be used to stiffen the protection assembly during insertion and to provide a tapered tip to facilitate blunt dissection as the protection sleeve assembly is inserted to the desired location adjacent to the proximal end of the tibia.

As shown in FIG. 26, a wire guide 450 according to an alternative embodiment includes a central lumen 452 that extends along a longitudinal axis of the wire guide 450 (coincident, in this embodiment, with a central axis of a protection sleeve 412 into which it is inserted). As described above, if it is determined that the position of the guide wire needs to be adjusted, the physician removes the wire guide 450 by withdrawing it over the guide wire until the guide wire exits the wire guide 450 and then re-inserts the guide wire into an offset lumen 454 that is radially offset from and parallel to the central lumen 452. The wire guide 450 is then passed over the guide wire through the protection sleeve 412 to the proximal surface of the tibia and rotated as desired until the central lumen 452 is aligned with a desired path along which it is desired to insert a second guide wire into the tibia. The second guide wire is then placed into the tibia via the central lumen 452 as desired and the first guide wire is removed. As shown in FIG. 26, a distal portion 456 of the wire guide 450 is formed as a portion of a cylinder with shaved planar sides 458.

In an alternative embodiment, the wire guide 450 is inserted directly through the incision to the tibia. A guide wire is inserted into the tibia through the wire guide 450, in a manner similar to that described above, and the protection sleeve 412 is inserted directly over the guide wire without using a trocar. The protection sleeve 412 is then fixed either to the tibia, the femur or both. After fixation of the protection sleeve 412, the wire guide 450 is removed. In such an embodiment, the wire guide 450 is made as slim as possible, i.e., a distal portion of the wire guide 450 has a reduced diameter with a blunt tip and flattened sides.

The distal portion 456 of this embodiment is sized to be as small as possible while accommodating the central lumen 452 and the offset lumen 454. This permits the protection sleeve assembly through which it has been inserted to partially collapse, further reducing trauma to the surrounding tissue. As would be understood by those skilled in the art, a length of the wire guide 450 is selected so that, when the wire guide 450 is fully inserted into a protection sleeve assembly, the distal end 460 of the wire guide 450 contacts the tibia while a proximal end 462 extends proximally out of the handle of a protection sleeve assembly through which it has been inserted. As can be seen in FIG. 26, the distal end 460 of the wire guide 450 is formed as a rounded concave end to facilitate blunt dissection of tissue so that this wire guide 450 may alternatively be used in place of the trocar 430 to facilitate insertion of the protection sleeve assembly over the guide wire to the target site at the proximal end of the tibia.

As shown in FIGS. 27-32, a core sleeve 500 of a further embodiment that may be employed within any of the protection sleeve assemblies described herein may be formed from two sheets 502 of a metal or other material similar to that described above in regard to the core sleeve 116. As seen in FIGS. 27-32, a core sleeve 500 according to this embodiment is formed by bending a pair of sheets 502 around a longitudinal axis L so that each sheet 502 forms one half of a generally tubular structure with the two halves being mirror images of one another. Each sheet 502 includes a plurality of receiving tabs 504 each of which defines a tab receiving opening 508 along a first lateral surface with a corresponding plurality of locking tabs 506 formed at corresponding locations along the axis L on the opposing lateral surface.

Figure 28A:
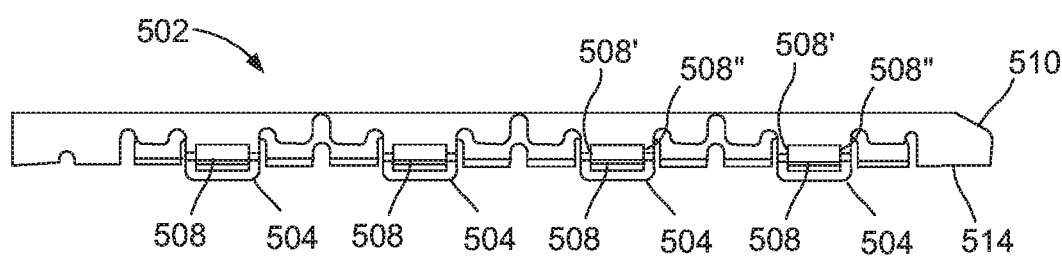
FIG. 28A shows a front view of the sheet of FIG. 27 bent into a preliminary shape for forming the core protection sleeve of FIGS. 30-32.
Figure 28B:
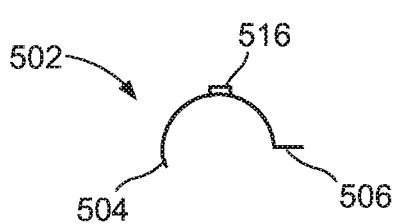
FIG. 28B shows a side view of the sheet of FIG. 27 bent into a preliminary shape for forming the core protection sleeve of FIGS. 30-32.
Figure 29:
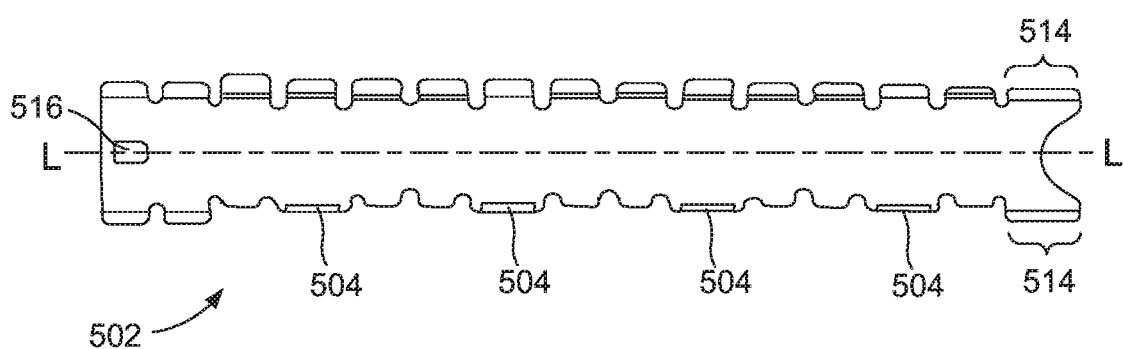
FIG. 29 shows a bottom view of the sheet of FIG. 27 bent into a preliminary shape for forming the core protection sleeve of FIGS. 30-32.

Each of the locking tabs 506 of a first one of the sheets 502 is sized and positioned to be received through the tab receiving opening 508 of a correspondingly located receiving tab 504 of the other sheet 502 after the sheets 502 have been bent into their half tubular shapes. As can be seen in FIGS. 28A, 28B and 29, after the sheets 502 of this embodiment have been bent into their generally half tubular shapes, the receiving tabs 504 extend generally along a tangent to the tube formed by the sheet 502 while the locking tabs 506 project radially outward away from the axis L. Thus, when the sheets 502 are assembled to form the generally tubular structure of the core sleeve 500, each locking tab 506 projects radially outward through the tab receiving opening 508 of its corresponding receiving tab 504.

Figure 30:
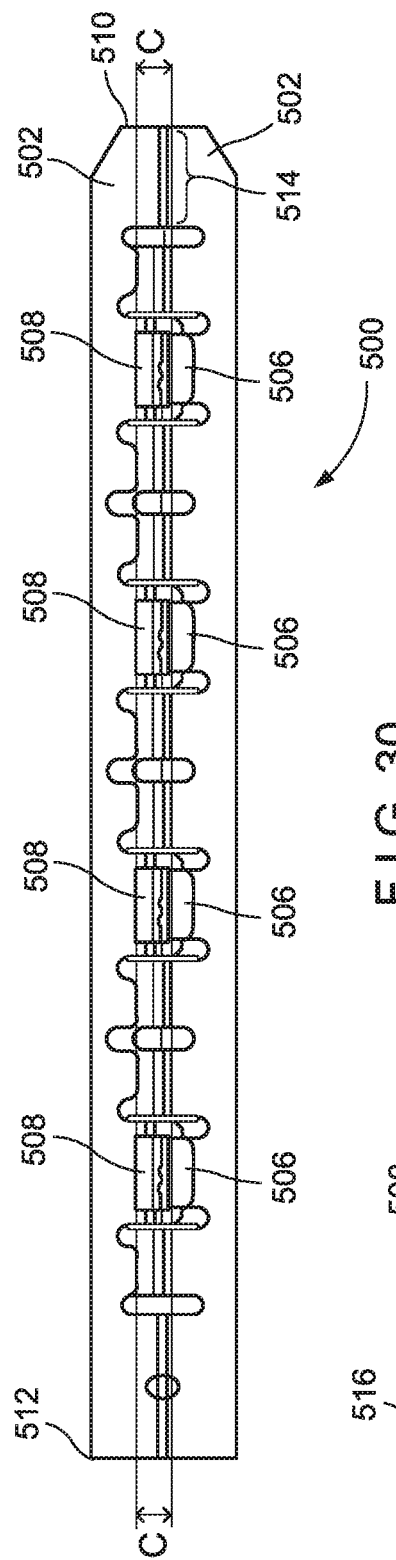
FIG. 30 shows a side view of a core protection sleeve formed from sheets as shown in FIG. 27.
Figure 31:
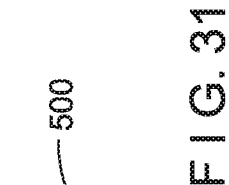
FIG. 31 shows a front view of a core protection sleeve formed from sheets as shown in FIG. 27.
Figure 32:
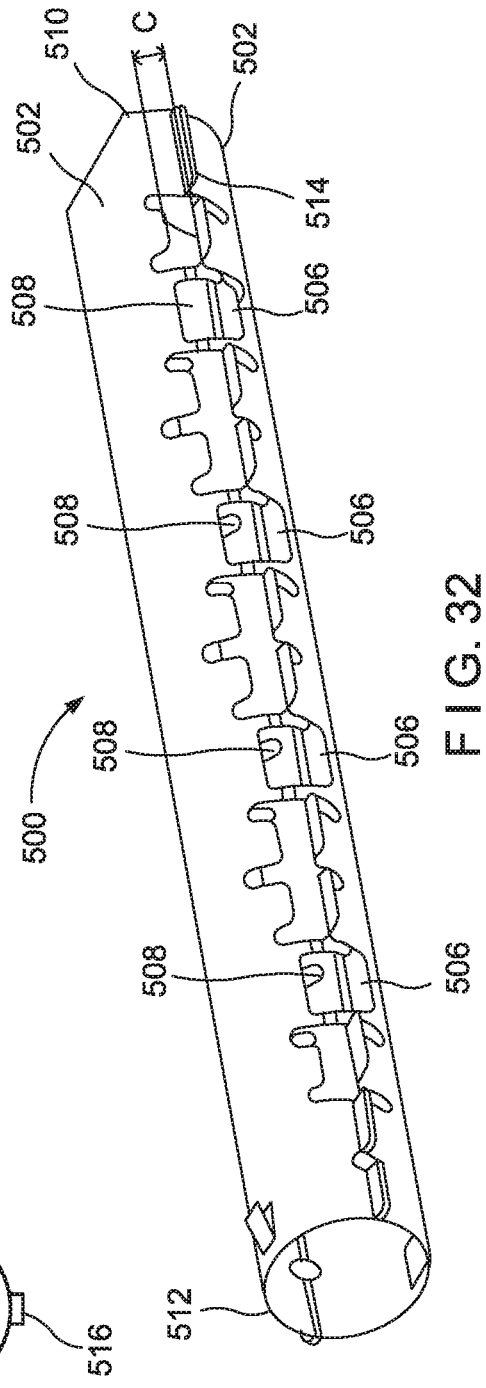
FIG. 32 shows a perspective view of a core protection sleeve formed from sheets as shown in FIG. 27.

In a subsequent operation, as shown in FIGS. 30-32, each locking tab 506 is then bent toward a position in which an outer ends of the locking tab 506 extends back toward its point of connection to the sheet 502 from which it extends substantially parallel to the receiving tab 504 through which it extends. This locks the two sheets 502 together while permitting the tubular structure of the core sleeve formed by the sheets 502 to contract under pressure from surrounding tissue in the same manner described above in regard to the other core sleeves. The range of this contraction C is defined by the dimension of the tab receiving openings 508 in the direction of the tangent to the tubular structure minus the thickness of the tab 506 (i.e., by the range of motion permitted to each of the tabs 506 within its corresponding tab receiving opening 508).

In addition, the two sleeves 502 are coupled to one another via, for example, welding at their distal ends 510 while the proximal ends 512 of the sheets 502 are not welded to one another. Specifically, the distal end 510 of this embodiment is laser welded along a seam 514. Those skilled in the art will understand that this will permit the tubular structure of the core sleeve according to this embodiment to expand more readily at its proximal end 512 as bent portions of an IM nail are forced therethrough.

In addition, the connection between the locking tabs 506 and the receiving tabs 504 enhances the resistance of the core sleeve according to this embodiment to shear forces to which the protection sleeve is subjected to from the patella-femoral joint as the bent IM nail is pushed through the protection sleeve. That is, as a bent IM nail is pushed through the protection sleeve, one half of the core sleeve (e.g., along an inner diameter of a bend in the IM nail) may be urged to migrate proximally within the protection sleeve while the other half of the core sleeve experiences forces urging it in the opposite direction. This sets up shear forces acting between the two sheets 502 which, in this embodiment are resisted by contact between the locking tabs 506 and the proximal end distal surfaces 508', 508", respectively, of the tab receiving openings 508 prevents migration of the sheets 502 relative to one another as the IM nail is inserted therethrough.

Moreover, the connection between the locking tabs 506 and the proximal end distal surfaces 508', 508", respectively, of the tab receiving openings 508 prevents radially outward expansion of the core sleeve, as the nail bend passes through, minimizing the pressure on the knee joint. In addition, each of the sheets 502 includes a tab 516 which, as described below, serve to lock the core sleeve to a handle to prevent the core sleeve from migrating distally within the protection sleeve as the IM nail is pushed distally therethrough.

Figure 33A:
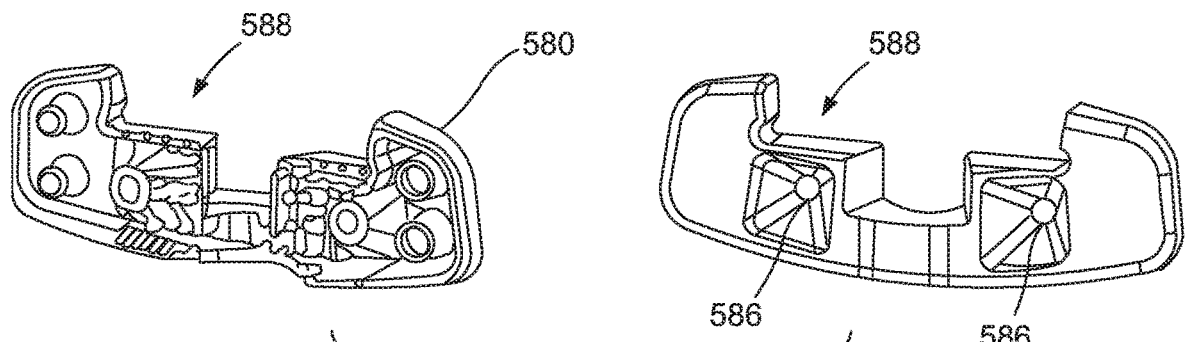
FIG. 33A shows a perspective view of a handle of a protection assembly according to an embodiment with halves of the handle separated from one another.
Figure 33B:
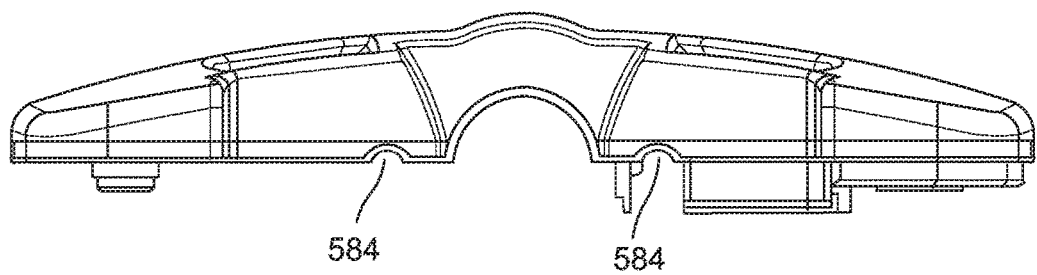
FIG. 33B shows a top view of one half of the handle of FIG. 33A.

As shown in FIGS. 33-37, a protection sleeve assembly 550 for use with, for example, the core sleeve 500, includes an outer sleeve 560, a handle 580, a locking ring 600 which couples the outer sleeve 560, the core sleeve 500 and the handle 580 to one another. As seen in FIG. 33, the handle 580 is formed of two halves coupled to one another to receives binding platforms 562 projecting laterally outward at the proximal end 564 of the sleeve 560. The binding platform 562 is received within a correspondingly sized and shaped cavity 582 formed between the halves of the handle 580. In addition, after the core sleeve 500 has been inserted into the outer sleeve 560, a locking ring 600 is seated within the proximal opening 564 with mounting posts 602 of the locking ring 600 received within wells 566 at either side of the opening 564 until a distal face 604 of each of the posts 602 resting on a proximally facing surface at the distal ends of the wells 566.

As the locking ring 600 is inserted distally into the opening 564, laterally projecting spurs 606 of the locking ring slide into the core sleeve 500 until each of the spurs 606 enters an opening under a corresponding one of the tabs 516 of the core sleeve 500 to lock the core sleeve 500 at a desired position within the outer sleeve 560. In this embodiment, the outer sleeve 560 includes no lateral guide wire lumens for tibial fixation. Thus, in this embodiment, the posts 602 project proximally out of the outer sleeve 560 to engage openings 584 in the handle 580 which, in embodiments including such tibial fixation guide wire lumens, would pass through the handle 580 to open to these guide wire lumens. As would be understood by those skilled in the art, the outer sleeve 560 of this embodiment may be substantially similar to any of the outer sleeves discussed above except for the structure at the proximal end serving to fix the outer sleeve 560 to the handle 580.

The locking ring 600 of this embodiment not only locks the core sleeve 500 at a desired position within the outer sleeve 560, it also serves to plug the tibial fixation guide wire openings in the handle 580. Those skilled in the art will understand that, for an outer sleeve including lateral guide wires for tibial fixation, the locking ring will be constructed similarly to the locking ring 600 except that the posts 602 will not be included so that the guide wire openings 584 are unobstructed. As would be understood, the guide wire lumens of such an outer sleeve would be positioned so that a guide wire inserted through either of the openings 584 in the handle 580 would pass through the handle 580 into the proximal opening of one of the lateral guide wire lumens and pass therethrough to the proximal surface of the tibia in the same manner described above.

Figure 34:
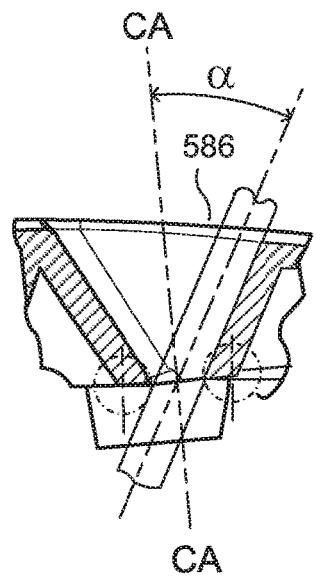
FIG. 34 shows a cross-sectional view of a guide wire opening of the handle of FIG. 33A.
Figure 35:
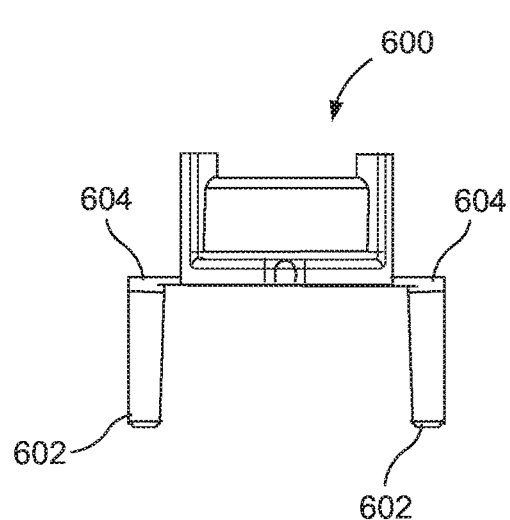
FIG. 35 shows a side view of a locking ring for use with the handle of FIG. 33A.
Figure 36:
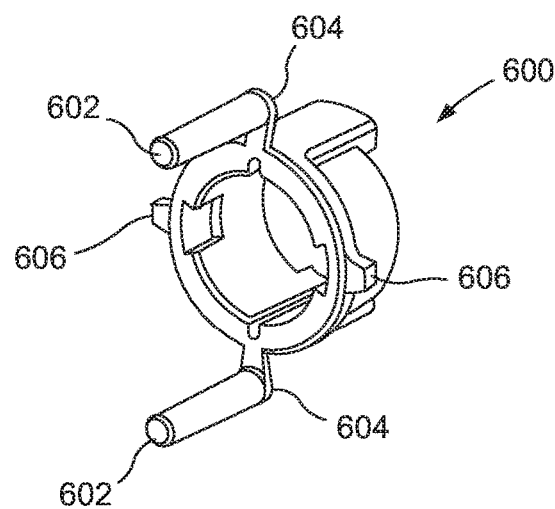
FIG. 36 shows a perspective view of the locking ring of FIG. 35.
Figure 37:
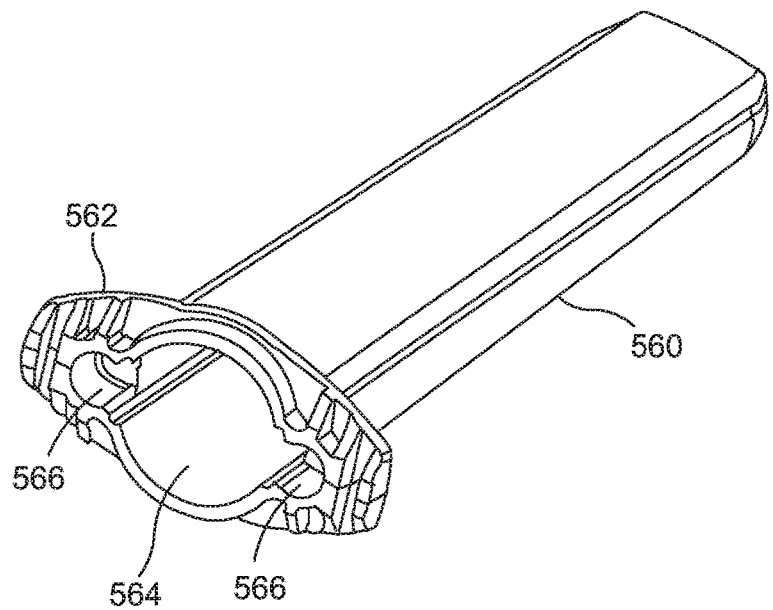
FIG. 37 shows an outer sleeve for use with an embodiment of a protection assembly including the handle of FIG. 33A and the locking ring of FIG. 35.

When the halves of the handle 580 are coupled to one another snapping over the binding platforms 562 to lock the outer sleeve 560 to the handle 580. As shown in FIGS. 33A and 34, the handle 580 includes two guide wire openings 586 aimed to permit insertion of guide wires into the femur to stabilize the protection sleeve assembly 500. As indicated in FIG. 34, each of the guide wire openings 586 is formed as a part of a cone having a vertex angle of 55 degrees (i.e., a guide wire is insertable through either of the openings 586 at an angulation of up to 27.5 degrees from a central axis CA of the opening 586 in any direction. However, those skilled in the art will understand that this angle α may be any desired value that permits the require femoral fixation. As indicated above, a recess 588 at a proximal end of the handle 580 is sized, shaped and structured to receive and locking in place a trocar as described above or any other device to be inserted through the central lumen of the assembly 550.

Although these embodiments have been described in connection with the suprapatellar insertion of a tibial IM nail, those skilled in the art will understand that this system would also be useful for spinal surgeries as well. In addition, although specific embodiments and methods have been described, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular applications of elements may be reversed or interposed, all without departing from the spirit or scope of the invention.

What is claimed is:

1. A device for facilitating an insertion into a living body of a bone treatment device, comprising:
    an outer sleeve of flexible material forming an outer conduit extending longitudinally therethrough for the insertion of the bone treatment device to target sites within the body, a distal opening of the outer conduit being open so that, when the outer sleeve is in a desired position within the body, the bone treatment device is inserted through the outer conduit and exits the outer sleeve adjacent to a target portion of a bone; and
    an inner sleeve received within the outer sleeve and defining an inner conduit within the outer conduit, the inner sleeve forming a protective covering within the outer conduit, the inner sleeve being formed of metal, the inner sleeve being split, portions of the inner sleeve on opposite sides of the split being coupled to one another so that a diameter of the inner conduit is adjustable within a predetermined range in response to forces exerted thereon by one of the bone treatment device and tissues surrounding the outer sleeve.

2. The device of claim 1, wherein the inner sleeve includes a first adjustment opening extending longitudinally along a portion of a length of the inner sleeve, a width of the first adjustment opening transverse to a longitudinal axis of the inner sleeve defining a maximum reduction in the diameter of the inner conduit as a diameter when opposing sides of the first adjustment opening contact one another.

3. The device of claim 2, wherein the inner sleeve is formed of first and second members, the first member including the first adjustment opening and a first sliding tab and the second member including a second adjustment opening and a second sliding tab, the first and second adjustment openings and the first and second sliding tabs being sized and positioned so that, when the first and second members are in a desired position relative to one another, the first sliding tab is slidably received within the first adjustment opening and the second sliding tab is slidably received in the second adjustment opening coupling the first and second members to one another, the first and second sliding tabs being slidable within the respective ones of the first and second adjustment openings transverse to the longitudinal axis of the first sleeve.

4. The device of claim 1, wherein the outer sleeve includes a first guide wire lumen extending longitudinally therealong aimed so that, when the device is in a desired position, a guide wire inserted through the first guide wire lumen passes into a portion of bone adjacent to the distal opening of the outer conduit to anchor the device in the desired position.

5. The device of claim 4, further comprising:
a handle mounted to a proximal end of the outer sleeve, the handle including a second guide wire lumen extending therethrough, the second guide wire lumen being aimed so that, when the device is in the desired position, a guide wire inserted therethrough will enter a non-targeted bone to fix the device to the non-targeted bone in the desired position relative to the target portion of the bone.

6. A system for treating a bone, comprising:
an insertion device configured for insertion within a living body, the insertion device providing a conduit to a target site within the body, the insertion device including an outer sleeve of flexible material forming an outer lumen extending longitudinally therethrough, a distal opening of the outer lumen being open so that, when the outer sleeve is in a desired position within the body a bone treatment device inserted through the outer lumen exits the outer sleeve adjacent to a target portion of the bone and an inner sleeve received within the outer sleeve and defining an inner lumen within the outer lumen, the inner sleeve forming a protective covering within the outer lumen, the inner sleeve being formed of metal, the inner sleeve being split longitudinally, portions of the inner sleeve on opposite sides of the split being coupled to one another so that a diameter of the inner lumen is adjustable within a predetermined range in response to forces exerted thereon by one of items inserted through the conduit and tissues surrounding the outer sleeve; and
a wire guide sized and shaped for insertion through the conduit to the target site, the wire guide including a first lumen extending along a central longitudinal axis of the wire guide, the first lumen being sized and shaped to slidably receive a guide wire therethrough, the wire guide including a second lumen laterally offset from and parallel to the first lumen, the second lumen being sized and shaped to slidably receive a guide wire therethrough.

7. The system of claim 6, wherein the outer sleeve includes a first guide wire lumen extending longitudinally therealong laterally outside the conduit, the first guide wire lumen aimed so that, when the insertion device is in the desired position, a guide wire inserted through the first guide wire lumen passes into a portion of bone adjacent to the distal end of the conduit to anchor the insertion device in the desired position.

8. The system of claim 7, wherein the insertion device further includes a handle mounted to a proximal end of the outer sleeve, the handle including a second guide wire lumen extending therethrough, the second guide wire lumen being aimed so that, when the device is in the desired position, a guide wire inserted therethrough will enter a non-targeted bone to fix the device to the non-targeted bone in the desired position relative to the target portion of the bone.

9. The system of claim 6, wherein the wire guide includes first and second generally planar surfaces connected to one another by arced surfaces mirroring a curvature of the inner lumen so that the wire guide is rotatable within the inner lumen, a thickness of the wire guide defined as a distance separating the generally planar surfaces being less than a diameter of the inner lumen so that, when the wire guide is received within the lumen, forces exerted on the outer sleeve by surrounding tissue compress the outer and inner sleeves toward the wire guide.

10. The system of claim 8, wherein the wire guide includes a distal end curved to form a blunt, rounded end to facilitate blunt dissection of tissue.

11. The system of claim 6, further comprising:
a trocar sized and shaped for insertion through the conduit, the trocar including a distal end curved to form a blunt, rounded end to facilitate blunt dissection of tissue when the trocar is inserted into the insertion device so that the blunt rounded end projects distally out of the outer sleeve.

12. The system of claim 11, wherein the insertion device further includes an insertion device handle mounted to a proximal end of the outer sleeve, the insertion device handle including a recess configured to lockingly receive a proximal handle of the trocar, a length of the trocar being selected so that, when the proximal handle of the trocar is lockingly received within the insertion device handle, the blunt rounded end of the trocar is in a desired position extending distally out of the outer sleeve.

13. The system of claim 6, wherein the insertion device further includes an insertion device handle mounted to a proximal end of the outer sleeve, wherein the inner sleeve includes a locking tab adjacent to a proximal end thereof, the system further including a locking ring received in a proximal end of the outer sleeve and extending into the handle to couple the outer sleeve to the handle, the locking ring including a locking projection sized and positioned so that, when the locking ring is positioned at a target position within the outer sleeve and the outer sleeve is mounted to the insertion device handle, the locking projection enters an opening at the locking tab to hold the inner sleeve at a desired position within the outer sleeve.

14. The system of claim 6, wherein the inner sleeve includes a first adjustment opening extending along a portion of a length of the inner sleeve, a width of the first adjustment opening transverse to a longitudinal axis of the inner sleeve defining a maximum reduction in the diameter of the inner lumen as a diameter when opposing sides of the first adjustment opening contact one another.

15. The system of claim 14, wherein the inner sleeve is formed of first and second members, the first member including the first adjustment opening and a first sliding tab and the second member including a second adjustment opening and a second sliding tab, the first and second adjustment openings and the first and second sliding tabs being sized and positioned so that, when the first and second members are in a desired position relative to one another, the first sliding tab is slidably received within the first adjustment opening and the second sliding tab is slidably received in the second adjustment opening coupling the first and second members to one another, the first and second sliding tabs being slidable within the respective ones of the first and second adjustment openings transverse to the longitudinal axis of the first sleeve.

16. The system of claim 15, wherein distal portions of the first and second members are bonded to one another and proximal portions of the first and second members are not bonded to one another.

17. The system of claim 16, wherein the distal portions of the first and second members are bonded to one another by welding.

18. The system of claim 17, wherein the proximal portions of the first and second members are free to move relative to one another limited by a linkage between the first sliding tab and the first adjustment opening and a linkage between the second sliding tab and the second adjustment opening.

* * * * *